(12) United States Patent
Yabusaki

(10) Patent No.: US 11,328,417 B2
(45) Date of Patent: May 10, 2022

(54) STORAGE DEVICE STORING A PROGRAM CAPABLE OF IMPROVING ACCURACY OF DETECTION OF A TARGET OBJECT

(71) Applicant: KOWA COMPANY, LTD., Nagoya (JP)

(72) Inventor: Katsumi Yabusaki, Tokyo (JP)

(73) Assignee: KOWA COMPANY, LTD., Nagoya (JP)

( * ) Notice: Subject to any disclaimer, the term of this patent is extended or adjusted under 35 U.S.C. 154(b) by 69 days.

(21) Appl. No.: 16/756,928

(22) PCT Filed: Oct. 29, 2018

(86) PCT No.: PCT/JP2018/040107
§ 371 (c)(1),
(2) Date: Apr. 17, 2020

(87) PCT Pub. No.: WO2019/088020
PCT Pub. Date: May 9, 2019

(65) Prior Publication Data
US 2020/0250818 A1    Aug. 6, 2020

(30) Foreign Application Priority Data

Oct. 30, 2017   (JP) .............................. JP2017-209546

(51) Int. Cl.
*G06T 7/00*     (2017.01)
*G06T 7/62*     (2017.01)

(52) U.S. Cl.
CPC .............. *G06T 7/0012* (2013.01); *G06T 7/62* (2017.01); *G06T 2207/30041* (2013.01)

(58) Field of Classification Search
CPC ...................... G06T 7/0012; G06T 7/62; G06T 2207/30041; G06T 2207/10076; G06T 2207/10101
See application file for complete search history.

(56) References Cited

U.S. PATENT DOCUMENTS

2016/0081663 A1*   3/2016  Chen ................... A61B 8/0866
                                                                600/425

FOREIGN PATENT DOCUMENTS

JP       H0984763       3/1997
JP      2010-514530     5/2010
(Continued)

OTHER PUBLICATIONS

PCT International Search Report for corresponding PCT Application No. PCT/JP2018/040107 (with translation), dated Jan. 15, 2019, 3 pages.
(Continued)

*Primary Examiner* — Siamak Harandi
(74) *Attorney, Agent, or Firm* — Dority & Manning, P.A.

(57) ABSTRACT

A non-transitory computer-readable medium stores a program capable of improving the accuracy of detection of a target object. The program causes a computer to execute operations including, acquiring data in which a physical quantity is associated with each unit area acquired by dividing a given space; setting a detection region in a time space of three or more dimensions in the space or the time space; setting a control region at a position surrounding a gap with the gap surrounding the detection region disposed in a space having the same dimensions as those of the detection region; and determined whether or not one or more unit areas included in the detection region are predetermined areas on the basis of comparison between physical quantities of one or more unit areas included in the detection region and the control region that are set.

18 Claims, 22 Drawing Sheets

(56) References Cited

FOREIGN PATENT DOCUMENTS

| JP | 2015-516192 | 6/2015 |
| JP | 2016-200444 | 12/2016 |
| WO | WO 2008/084352 | 7/2008 |
| WO | WO 2013/142176 | 9/2013 |
| WO | WO 2016/161198 | 10/2016 |

OTHER PUBLICATIONS

Yabusaki, Katsumi, Joshua D. Hutcheson, Payal Vyas, Sergio Bertazzo, Simon C. Body, Masanori Aikawa, and Elena Aikawa. 2016. "Quantification of Calcified Particles in Human Valve Tissue Reveals Asymmetry of Calcific Aortic Valve Disease Development." Frontiers in Cardiovascular Medicine 3 (1):44.doi:10.3389/fcvm.2016.00044. http://dx.doi.org/10.3389/fcvm.2016.00044.—11 pages.
Legland et al., "MorphoLibJ User Manual," Sep. 9, 2017, retrieved from https://github.com/ijpb/MorphoLibJ/releases/download/v.1.3.3/MorphoLibJ-manual-v1.3.3.pdf—64 pages.
Supplementary European Search Report for corresponding EP Application No. EP 18 87 3441.2, dated Aug. 18, 2021, 6 pages.

\* cited by examiner

| X COOR-DINATE | Y COOR-DINATE | Z COOR-DINATE | PREDETERMINED AREA FLAG |
|---|---|---|---|
| 0001 | 0001 | 0001 | 1 |
| 0001 | 0001 | 0002 | 1 |
| 0001 | 0001 | 0003 | 0 |
| ... | ... | ... | ... |
| 0001 | 0002 | 0001 | 1 |
| 0001 | 0002 | 0002 | 0 |
| 0001 | 0002 | 0003 | 0 |
| ... | ... | ... | ... |
| 0002 | 0001 | 0001 | 1 |
| 0002 | 0001 | 0002 | 1 |
| 0002 | 0001 | 0003 | 1 |
| ... | ... | ... | ... |

STORAGE DEVICE STORING A PROGRAM CAPABLE OF IMPROVING ACCURACY OF DETECTION OF A TARGET OBJECT

TECHNICAL FIELD

The present invention relates to an analysis device, an analysis method, and a storage medium.

BACKGROUND ART

Devices that image objects two-dimensionally or three-dimensionally are used. Such devices, for example, include various device including an optical microscope such as a laser scanning microscope, a confocal laser scanning microscope, or a fluorescence microscope, an electron microscope such as a transmission electron microscope (TEM) or a scanning electron microscope (SEM), and a tomographic imaging device that images a tomographic image of an object using optical coherence tomography (OCT), computed tomography (CT), positron emission tomography (PET), magnetic resonance imaging (MRI), nuclear magnetic resonance (NMR), ultrasonic waves, or the like. Such devices, for example, are used for imaging affected sites of patients and the like at medical sites.

PRIOR ART DOCUMENTS

Patent Document

Patent Document 1; Japanese Unexamined Patent Application, First Publication No. H9-84763

Non Patent Document

Non Patent Document 1: Yabusaki, Katsumi, Joshua D. Hutcheson, Payal Vyas, Sergio Bertazzo, Simon C. Body, Masanori Aikawa, and Elena Aikawa, 2016. "Quantification of Calcified Particles in Human Valve Tissue Reveals Asymmetry of Calcific Aortic Valve Disease Development." Frontiers in Cardiovascular Medicine 3 (1): 44.doi: 10.3389/fcvm.2016.00044, http://dx.doi.org/10.3389/fcvm.2016.00044.

SUMMARY OF INVENTION

Problems to be Solved by the Invention

However, in a conventional technology, there are cases in which a target object cannot be detected with high accuracy in a case in which the target object desired to be detected is minute.

The present invention is in view of such situations, and one object thereof is to provide an analysis device, an analysis method, and a program capable of improving accuracy of detection of a target object.

Solution to Problem

The present invention solving the problem described above is modified for allowing a concept of the method disclosed in Non-Patent Document 1 to be applicable also to a three-dimensional time space (a three-dimensional space or a two-dimensional space and a time axis) or a four-dimensional time space acquired by adding a time axis to a three-dimensional space, and one aspect thereof is an analysis device including: an acquirer that is configured to acquire data in which a physical quantity is associated with each unit area acquired by dividing a three-dimensional space, a three-dimensional time space, or a four-dimensional time space; a setter that is configured to set a detection region in a time space of three or more dimensions in the space or the time space and is configured to set a control region at a position surrounding a gap with the gap surrounding the detection region disposed in a space having the same dimensions as those of the detection region; and a determiner that is configured to determine whether or not one or more unit areas included in the detection region are predetermined areas on the basis of comparison between physical quantities of one or more unit areas included in the detection region and the control region set by the setter.

Advantageous Effects of Invention

According to the present invention, accuracy of detection of a target object can be improved.

BRIEF DESCRIPTION OF THE DRAWINGS

FIG. 5 is a diagram showing one example of scanning position information 214.

DESCRIPTION OF EMBODIMENTS

Hereinafter, an analysis device, an analysis method, and a program according to embodiments of the present invention will be described with reference to the drawings.

Overview

An analysis device according to an embodiment acquires volume data in which a physical quantity is associated with each unit region acquired by dividing a three-dimensional space, a three-dimensional time space, or a four-dimensional time space, setting a detection region that is a time space of three or more dimensions within this volume data, and setting one or a plurality of control regions at positions further surrounding a gap surrounding the detection region.

The volume data, for example, is data in which a three-dimensional space having width, height, and depth as its dimensions is divided for every certain unit region (hereinafter referred to as a voxel), and a physical quantity is associated with each voxel acquired through division. A physical quantity is a scalar value or a vector value and, for example, is an intensity of reflected light of laser light, an intensity of reflected waves of electromagnetic waves (electric waves, electrons, and the like), an intensity of reflective waves of sound waves, pixel values (luminance values or the like) of an image, a pressure, a flow rate, a temperature, an absorption spectrum, or the like. In addition, volume data, for example, may be data acquired by dividing a three-dimensional time space having arbitrary two out of the three elements of width, height, and depth as its dimensions for every voxel, data acquired by dividing a four-dimensional time space having width, height, depth, and time as its dimensions for every voxel (or a dynamic voxel), or data acquired by dividing a multi-dimensional space handling different elements as dimensions for every voxel.

The analysis device determines whether one or more voxels included in a detection region are predetermined areas on the basis of comparison between physical quantities of one or more voxels included in individual detection regions and control regions and evaluates an observation target observed when volume data is generated on the basis of a result of the determination.

First Embodiment

[System Configuration]

Figure 1:
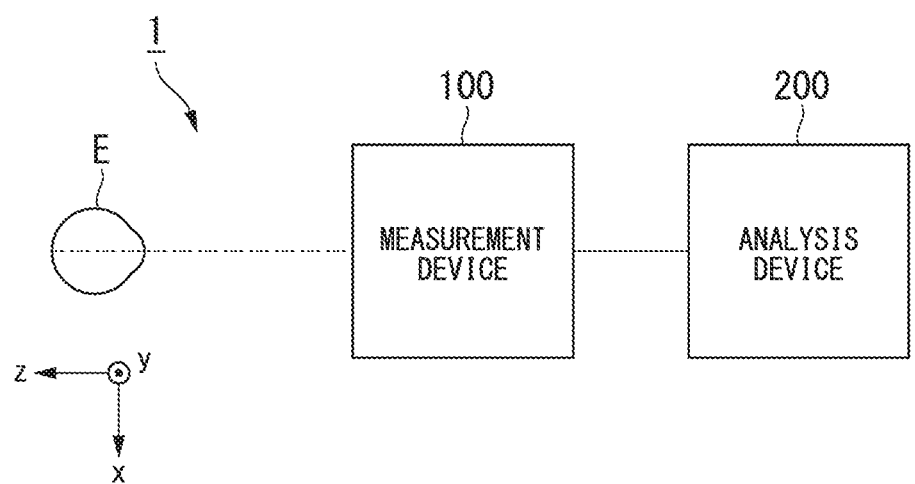
FIG. 1 is a diagram showing one example of the configuration of an inspection system 1 including an analysis device 200 according to a first embodiment.

FIG. 1 is a diagram showing one example of the configuration of an inspection system 1 including an analysis device 200 according to a first embodiment. The inspection system 1, for example, is a system that inspect eyeballs E of humans or other animal. For example, the inspection system 1 includes a measurement device 100 and an analysis device 200. For example, the measurement device 100 emits laser light to the inside of an anterior chamber of an eyeball E that is a test object, receives scattered light (reflected light) of the emitted laser light, and provides information representing a result of the reception of light for the analysis device 200. The anterior chamber is a region between an iris and an endothelial cell of an innermost layer of a cornea and is filled with a liquid called aqueous humor. The analysis device 200 acquires the number of biological cells (cells) present inside the anterior chamber of the eyeball E on the basis of the information provided by the measurement device 100 and evaluates a state of the eyeball E. Hereinafter, an emission direction (a depth direction of the eyeball E) of the laser light will be represented as a z direction (axis), one direction orthogonal to the z direction will be represented as an x direction (axis), and a direction orthogonal to both the z direction and the x direction will be represented as a y direction (axis) in the description. In other words, the z direction represents a depth direction in a three-dimensional space, the x direction represents one of a width direction and a height direction in the three-dimensional space, and the y direction represents the other of the width direction and the height direction in the three dimensional space. In addition, any one of the x direction, the y direction, and the z direction may be in a dimension of time (t direction).

[Configuration of Measurement Device]

Figure 2:
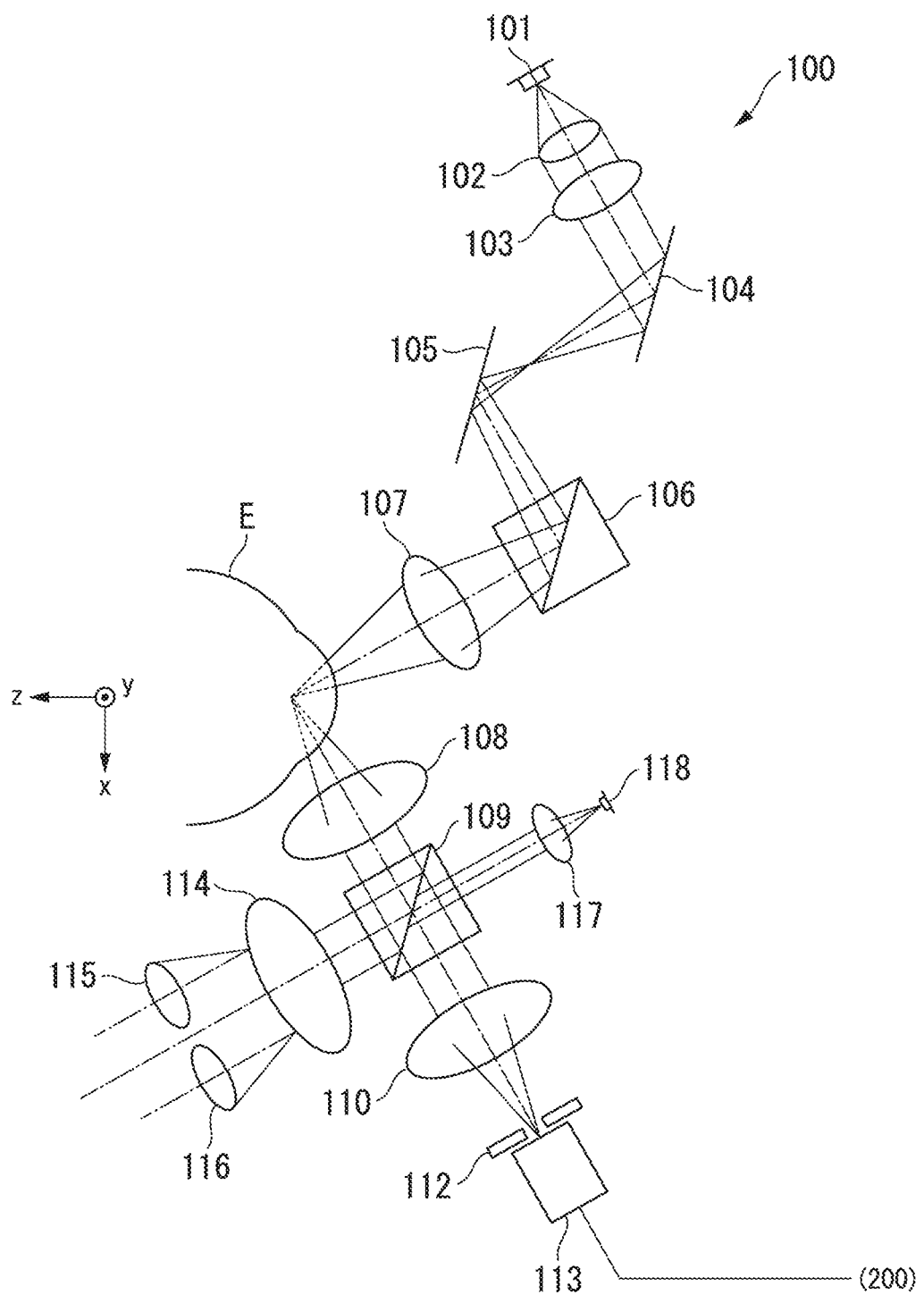
FIG. 2 is a diagram showing one example of the configuration of a measurement device 100.

FIG. 2 is a diagram showing one example of the configuration of the measurement device 100. The measurement device 100, for example, includes a first light source 101, lenses 102, 103, 107, 108, 110, and 114 to 117, galvanometer mirrors 104 and 105, a prism 106, a half mirror 109, a light reception mask 112, a photomultiplier tube 113, and a second light source 118. For example, the first light source 101 is a laser light source that emits laser light, and the second light source 118 is a light emitting diode (LED) that emits visible light such as red light.

The laser light emitted by the first light source 101 expands into parallel light or the like at the lenses 102 and 103 and is incident on the galvanometer mirror 104. The laser light incident on the galvanometer mirror 104 is reflected by a mirror surface of the galvanometer mirror 104 and is incident on the galvanometer mirror 105. The laser light incident on the galvanometer mirror 105 is reflected by a mirror surface of the galvanometer mirror 105 and is incident on the prism 106. The laser light incident on the prism 106 is condensed into the inside of the anterior chamber of the eyeball E through the lens 107. At this time, the galvanometer mirror s 104 and 105 are driven by driving mechanisms not shown in the drawing, and an angle of the mirror surface with respect to an incidence angle of the laser light is changed. For example, the galvanometer mirror 104 contributes to horizontal scanning (in the x direction) of the laser light inside the anterior chamber, and the galvanometer mirror 105 contributes to a vertical scanning (in the y direction). In this way, the laser light condensed into the inside of the anterior chamber of the eyeball E is two-dimensionally scanned in the x direction and the y direction.

Some of the laser light condensed into the inside of the anterior chamber of the eyeball E is reflected as scattered light. For example, in a case in which biological substances such as protein molecules and cells float inside the anterior chamber, some of the laser light is reflected by the biological substances. The scattered light reflected from the anterior chamber is converted into parallel light after being condensed by the lens 108 and is incident on the half mirror 109. Some of the light that is incident on the half mirror 109 is transmitted through the half mirror 109 and is guided to the lens 110 side, and the remaining light that is incident on the half mirror 109 is reflected by the half mirror 109 and is guided to the lens 114 side. The scattered light that has been transmitted through the half mirror 109, after being condensed by the lens 110, passes through the light reception mask 112 used for limiting a field of vision, and the light that has passed is incident on the photomultiplier tube 113. The light reception mask 112, for example, is a pinhole having a circular opening. In accordance with this, only light at an in-focused position is incident on the photomultiplier tube 113. The photomultiplier tube 113 converts incident light into a discrete electric signal using a photo counting technique. Then, the photomultiplier tube 113 outputs the converted electric signal to the analysis device 200.

The scattered light reflected by the half mirror 109 is diffused or condensed by the lens 114 and is incident on a user's eye to be inspected through the lenses 115 and 116. The light emitted by the second light source 118, after being diffused or condensed by the lens 117, passes through the half mirror 109 and is incident on the user's eye. The lens 117 is installed at a position for forming an image of the light emitted by the second light source 118 at a conjugate position for the light reception mask 112. In accordance with this, for example, by forming an image of a window having a frame shape in accordance with light according to the second light source 118, a user is able to visually recognize a relative position of a biological object reflecting scattered light with respect to the window.

The measurement device 100 moves a scanning position of the laser light in the z direction that is the depth direction of the anterior chamber by two-dimensionally (in the x and y directions) scanning laser light (x-y directions) by driving the galvanometer mirrors 104 and 105 and then moving the position of the light reception mask 112 in an optical axis direction of light that has passed through the lens 110. In accordance with this, the anterior chamber of the eyeball E is three-dimensionally measured.

In addition, the measurement device 100 may further include a stage that moves the position of the optical system described above in the z direction. In such a case, when the laser light two-dimensionally (in the x and y directions) scans (the x-y directions) by driving the galvanometer mirrors 104 and 105, the measurement device 100 may change the scanning position of the laser light by moving the stage in the z direction instead of moving the position of the light reception mask 112.

[Configuration of Analysis Device]

Figure 3:
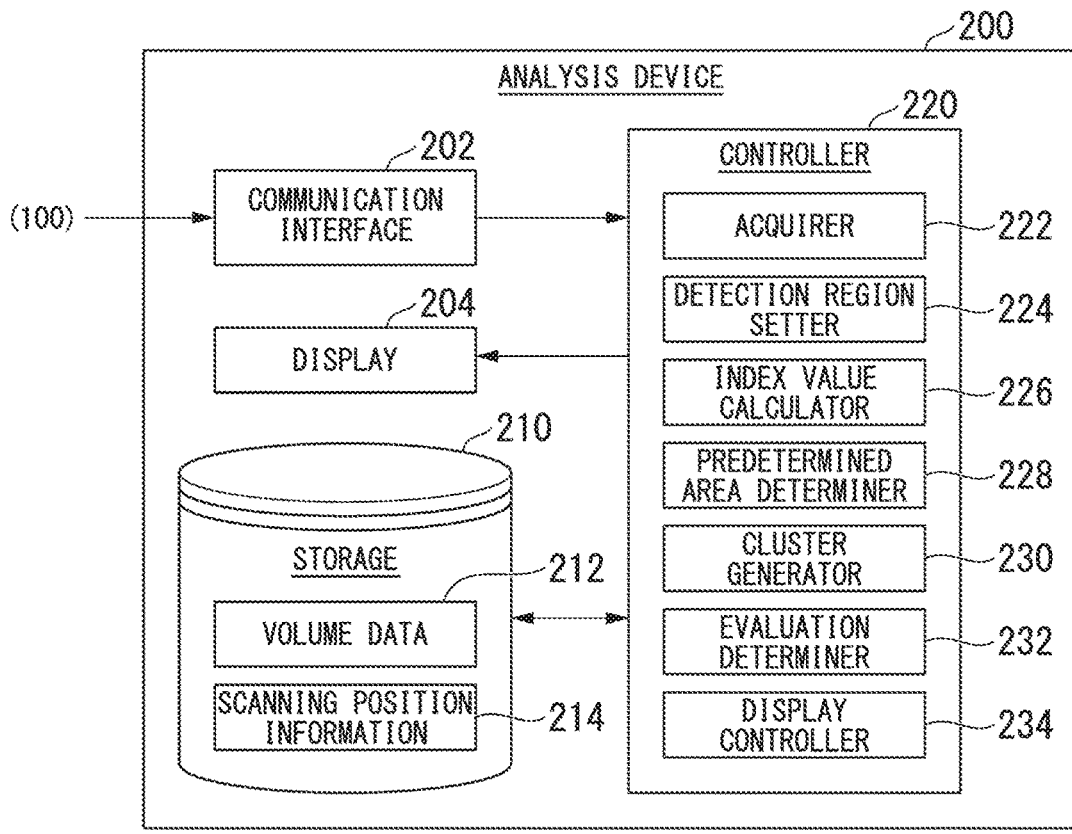
FIG. 3 is a diagram showing one example of the configuration of an analysis device 200.

FIG. 3 is a diagram showing one example of the configuration of the analysis device 200. As in the example shown in the drawing, the analysis device 200 includes a communication interface 202, a display 204, a storage 210, and a controller 220.

The communication interface 202, for example, communicates with the measurement device 100 in a wired or wireless manner. In addition, the communication interface 202 may communicate with devices other than the measurement device 100.

The display 204, for example, is a display device such as a liquid crystal display (LCD), an organic electroluminescence (EL) display, or the like.

The storage 210, for example, is realized by a hard disk drive (HDD), a flash memory, an electrically erasable programmable read only memory (EEPROM), a read only memory (ROM), a random access memory (RAM), or the like. The storage 210, for example, stores a program that is referred to by the controller 220, the volume data 212, scanning position information 214, and the like.

Figure 4:
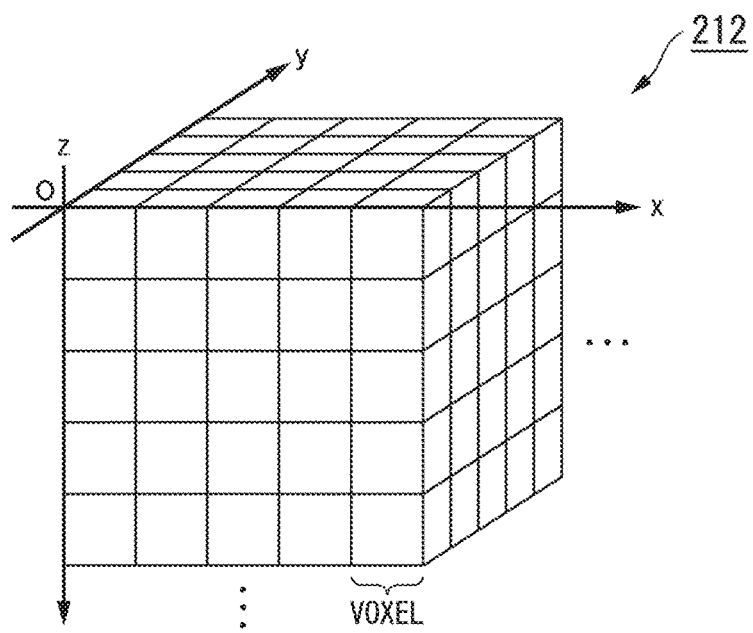
FIG. 4 is a diagram schematically showing volume data 212.

FIG. 4 is a diagram schematically showing the volume data 212. As shown in the drawing, the volume data 212 according to the first embodiment is data in which a signal intensity value of an electric signal converted from scattered light, in other words, an intensity of the scattered light is associated with each voxel included in a three-dimensional space having the width direction x, the height direction y, and the depth direction z as its dimensions. Hereinafter, a physical quantity associated with a voxel will be referred to as a voxel value in the description. In addition, in the example shown in the drawing, although a voxel is represented as a three-dimensional space having a certain volume, the voxel may be represented as a point having no dimensions (zero dimensions). In a case in which a voxel is represented as a point, the volume data 212 may be data having a multi-dimensional array structure in which physical quantities are stored as elements of the array.

FIG. 5 is a diagram showing one example of the scanning position information 214. The scanning position information 214 is information relating to a setting position of each detection region Ra to be described later and is information in which a predetermined area flag is associated with individual coordinates in a space represented by the volume data 212. A predetermined area flag is a flag that indicates whether a voxel of individual coordinates is a predetermined area using a binary value. In this embodiment, biological cells floating in aqueous humor that fills the anterior chamber of the eyeball E are set as observation targets, and accordingly, a predetermined area is defined as an area in which biological cells are present.

For example, when a certain detection region Ra is set in the space represented by the volume data 212, in a case in which a space region overlapping this detection region Ra is determined to be a predetermined area, a flag "1" is associated with coordinates of each of one or more voxels included in the space region, and otherwise, a flag "0" is associated with the coordinates. At this time, it is assumed that a predetermined area flag of the coordinates of each voxel is associated with "0" in advance before determination of whether it is a predetermined area or not. This process is performed for every change in the position of the detection region Ra (the position is shifted), and finally, a voxel to which the flag "1" is assigned (a voxel of which a flag is rewritten from "0" to "1") at least once is regarded as a voxel that is a predetermined area, and the predetermined area flag shown in FIG. 5 becomes "1". In other words, in a case in which the predetermined area flag is changed from "0" to "1" at least once, the flag is maintained in the state of "1."

The controller 220, for example, includes an acquirer 222, a detection region setter 224, an index value calculator 226, a predetermined area determiner 228, a cluster generator 230, an evaluation determiner 232, and a display controller 234. Some or all of such constituent elements are realized by a processor such as a central processing unit (CPU), a graphics processing unit (GPU), or the like executing a program stored in the storage 210. In addition, some or all of the constituent elements of the controller 220 may be realized by hardware such as a large scale integration (LSI), an application specific integrated circuit (ASIC), a field-programmable gate array (FPGA), or the like or may be realized by software and hardware in cooperation.

Figure 6:
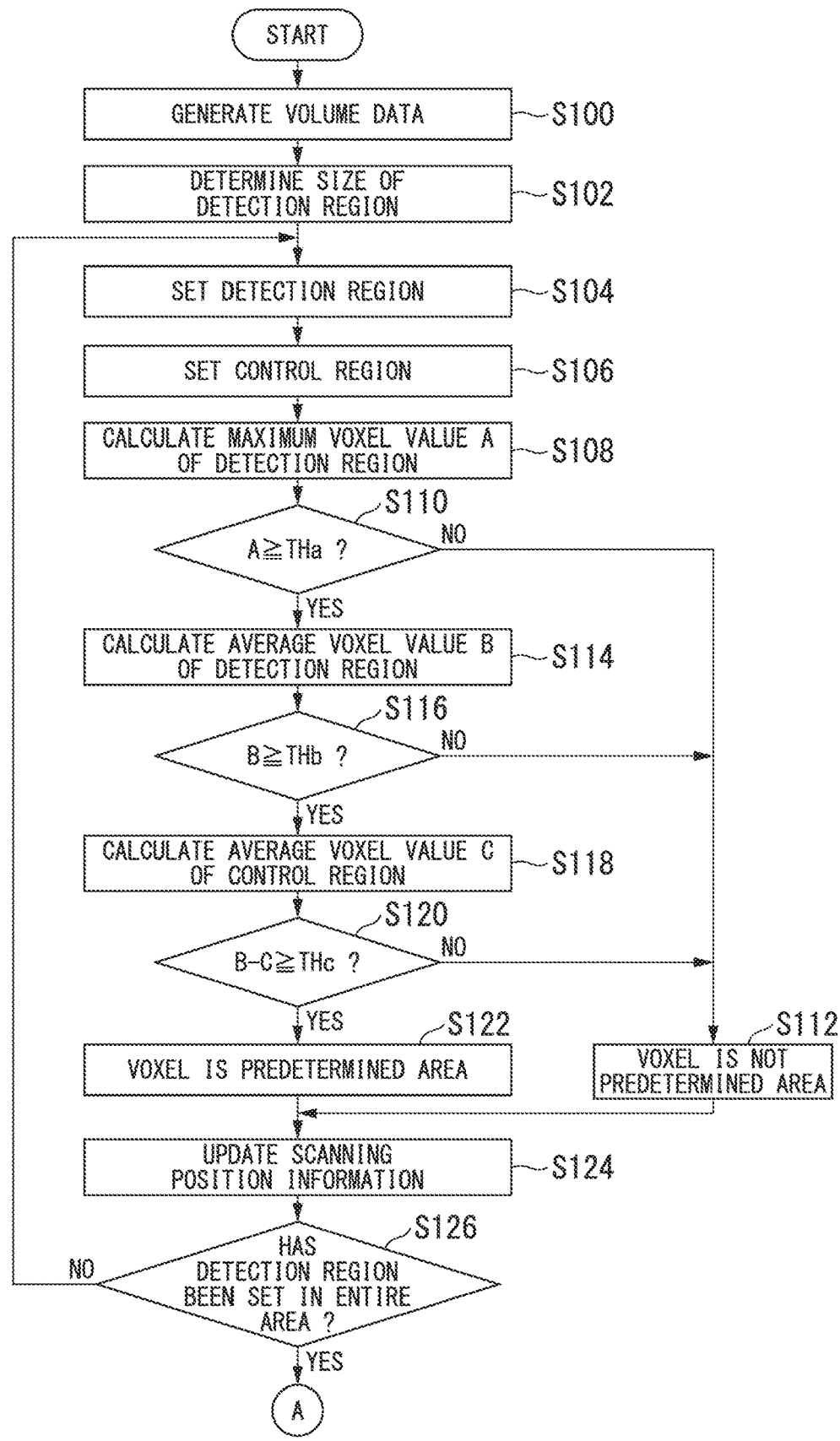
FIG. 6 is a flowchart showing one example of a series of processes according to a controller 220.
Figure 7:
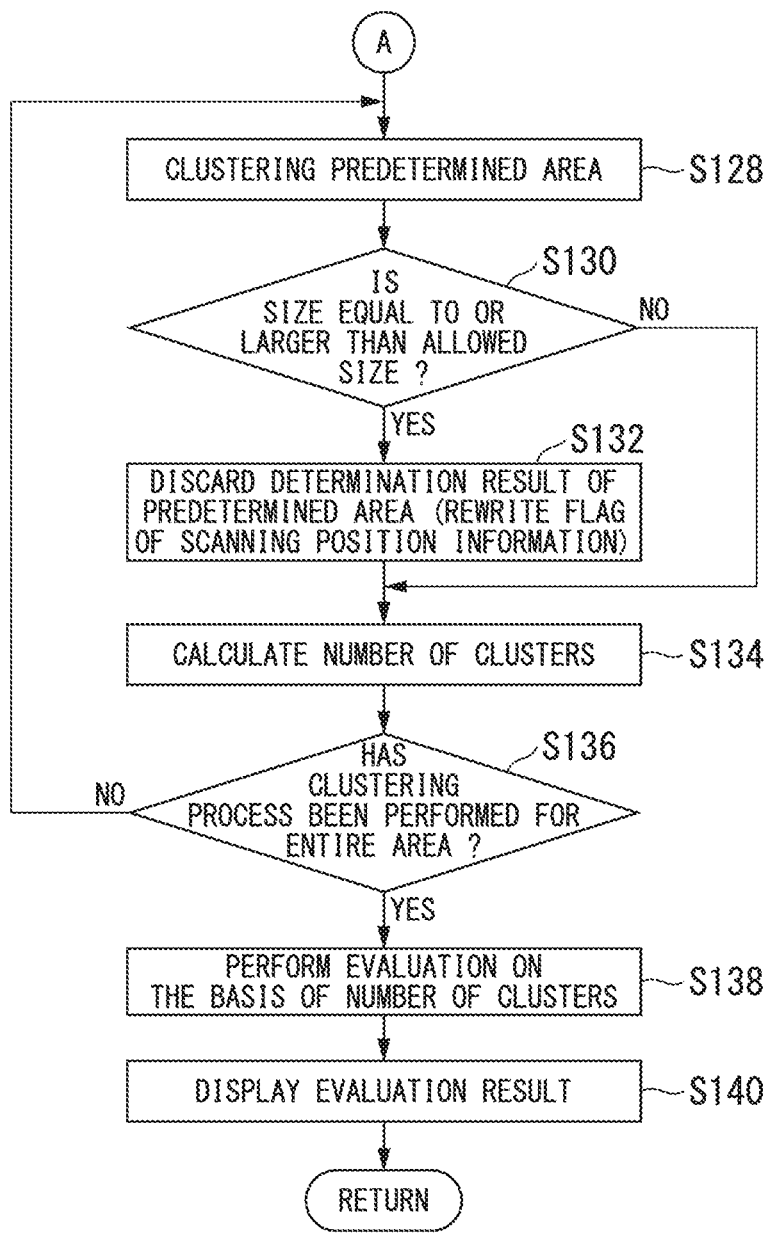
FIG. 7 is a flowchart showing one example of a series of processes according to the controller 220.

Hereinafter, a series of processes according to the controller 220 will be described with reference to a flowchart. FIGS. 6 and 7 represent a flowchart showing one example of a series of processes according to the controller 220. For example, the process of this flowchart is executed when an electric signal is acquired from the measurement device 100 or any other device through the communication interface 202. In addition, the process of this flowchart may be repeatedly performed at a predetermined period.

First, when an electric signal is acquired from the measurement device 100 through the communication interface 202, the acquirer 222 generates volume data 212 on the basis of this signal (Step S100) and stores the generated volume data in the storage 210. In addition, the process of generating the volume data 212 may be performed on the measurement device 100 side. In such a case, the acquirer 222 may acquire the volume data 212 from the measurement device 100. In addition, in a case in which the volume data 212 that has already been generated is stored in an external storage device such as a cloud server or the like, the acquirer 222 may acquire the volume data 212 from this device by communicating with the external storage device through the communication interface 202.

Next, the detection region setter 224 determines a size of the detection region Ra in accordance with a resolution of the volume data 212 (a density of the voxel for the volume data 212). Here, "the determining of a size", for example, involves determining a length of a region of each dimension or an area, a volume, or the like of the region.

For example, in a case in which a space represented by the volume data 212 is a three-dimensional space represented by x-y-z, the detection region setter 224 sets a length of each side including width, height, and depth of the detection region Ra smaller as the resolution of the volume data 212 becomes higher and sets the length of each side including the width, the height, and the depth of the detection region Ra larger as the resolution of the volume data 212 becomes lower. In addition, the detection region setter 224 may determine a size of the detection region Ra such that it has a volume that is an integral multiple of the voxel that is a unit region of the volume data 212. In addition, the detection region setter 224 may determine lengths of some sides among the width, the height, and the depth regardless of the resolution of the volume data 212. In addition, it is assumed that the shape of the detection region Ra (a ratio among lengths of the sides) is determined in advance.

Next, the detection region setter 224 sets a detection region Ra of the determined size at an arbitrary position in the space represented by the volume data 212 (Step S104).

Next, the detection region setter 224 sets one or more control regions Rb such that they surround the set detection region Ra with a certain predetermined gap disposed therebetween (Step S106). Here, "surround" means that the detection region Ra enters a closed space formed by one or a plurality of control regions Rb in a partial space of a space in which at least the detection region Ra is set. For example, when the detection region Ra is a hexahedron such as a cube, in a case in which one cross section of the hexahedron enters a closed space formed by one or a plurality of control regions Rb, the control regions Rb surround the detection region Ra.

Figure 8A:
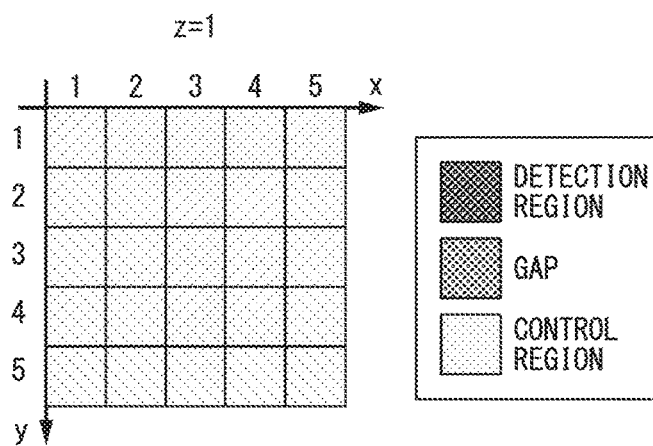
FIG. 8A is a diagram showing one example of a setting position of a detection region Ra.
Figure 8B:
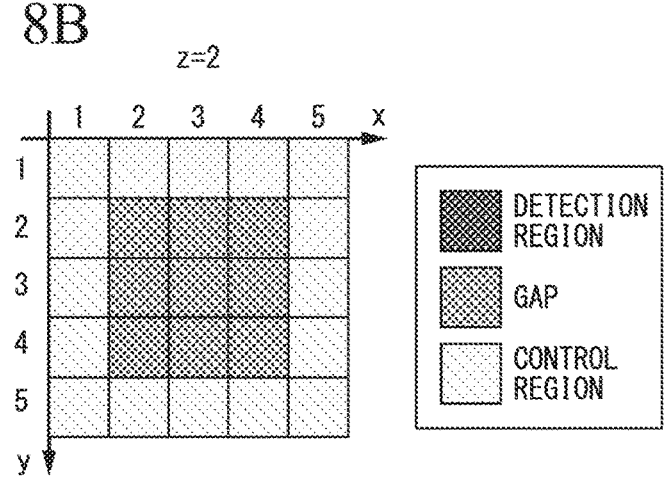
FIG. 8B is a diagram showing one example of a setting position of a detection region Ra.
Figure 8C:
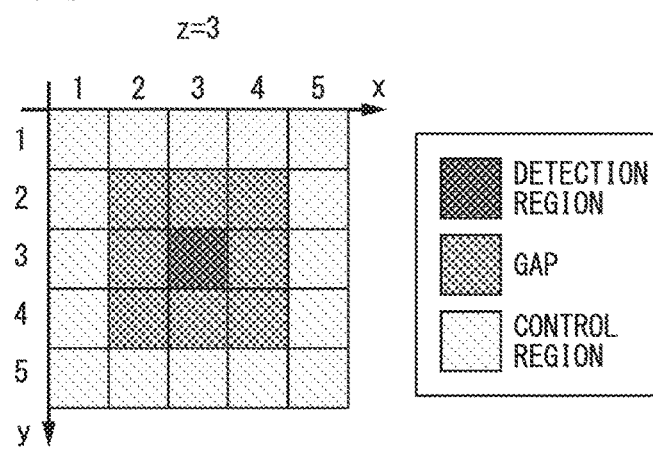
FIG. 8C is a diagram showing one example of a setting position of a detection region Ra.
Figure 8D:
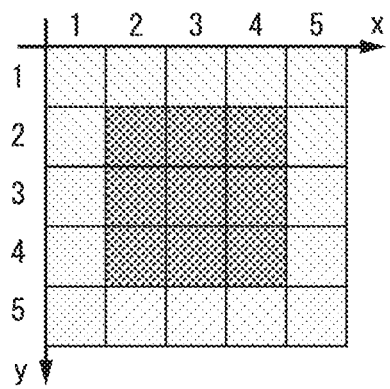
FIG. 8D is a diagram showing one example of a setting position of a detection region Ra.
Figure 8D:
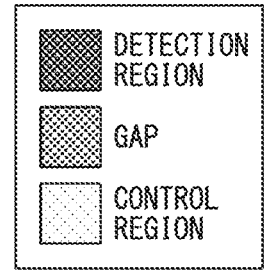
Figure 8E:
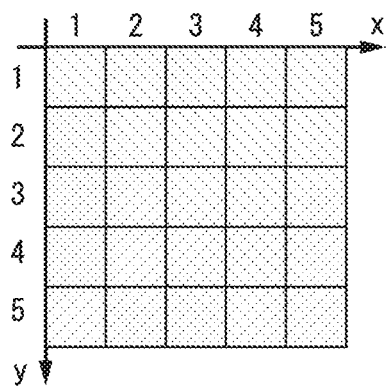
FIG. 8E is a diagram showing one example of a setting position of a detection region Ra.
Figure 8E:
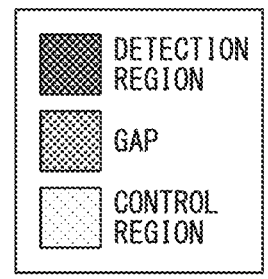

FIGS. 8A to 8F are diagrams showing one example of a setting position of a detection region Ra. FIGS. 8A to 8E show an x-y plane that is a partial space of an x-y-z space represented by the volume data 212. FIG. 8A shows an x-y plane having z=1, FIG. 8B shows an x-y plane having z=2, FIG. 8C shows an x-y plane having z=3, FIG. 8D shows an x-y plane having z=4, and FIG. 8E shows an x-y plane having z=5. In addition, in the example shown in the drawing, each voxel is represented as a cube of which lengths of sides of x, y, and z are "1." Furthermore, here, in a case in which a "plane" is mentioned, a length in the z direction corresponding to one voxel may be a unit length (for example, "1").

Figure 8F:
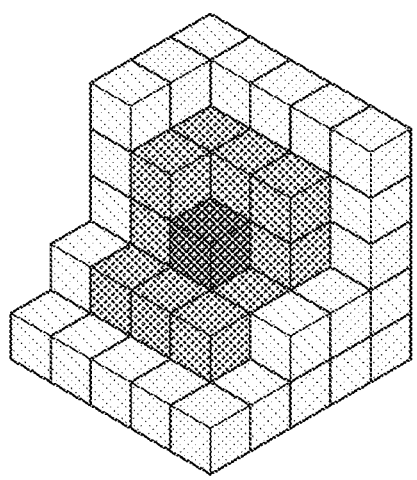
FIG. 8F is a diagram showing one example of a setting position of a detection region Ra.
Figure 8F:
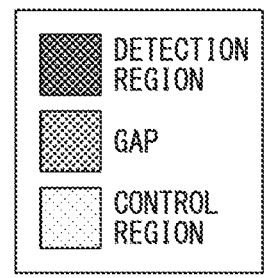
Figure 9A:
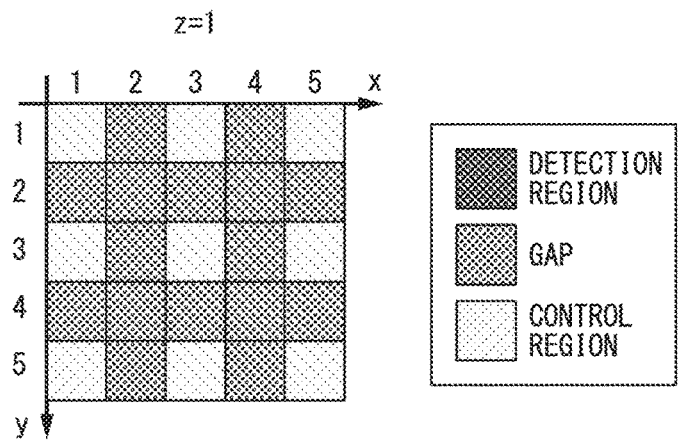
FIG. 9A is a diagram showing another example of a setting position of a detection region Ra.
Figure 9B:
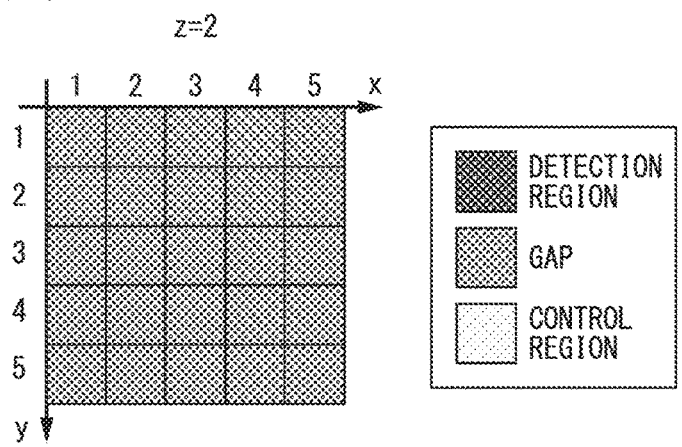
FIG. 9B is a diagram showing another example of a setting position of a detection region Ra.
Figure 9C:
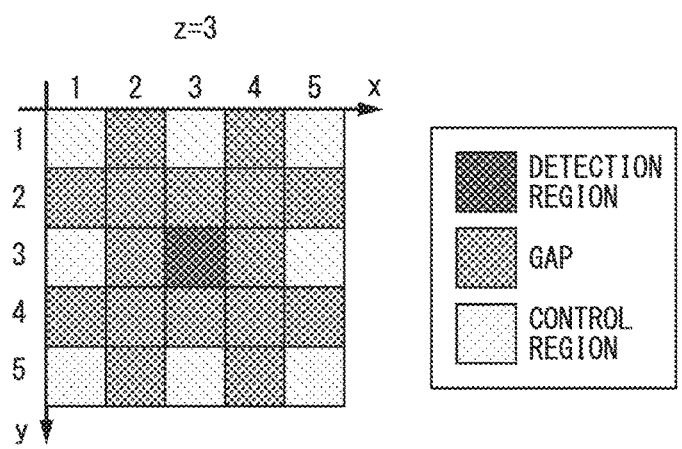
FIG. 9C is a diagram showing another example of a setting position of a detection region Ra.
Figure 9D:
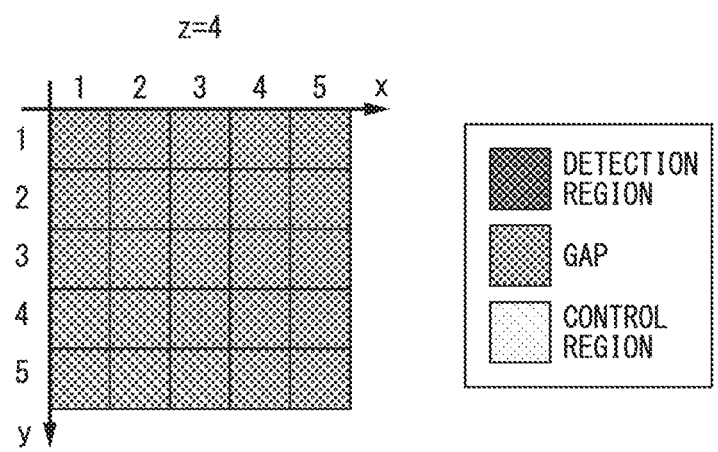
FIG. 9D is a diagram showing another example of a setting position of a detection region Ra.
Figure 9E:
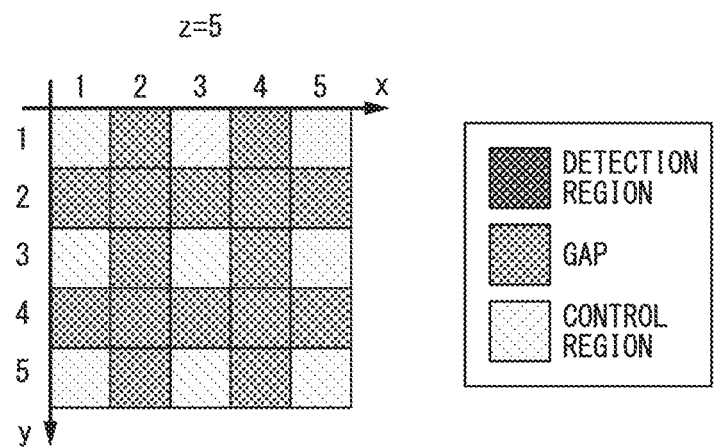
FIG. 9E is a diagram showing another example of a setting position of a detection region Ra.

For example, in a case in which a detection region Ra having the same volume as that of one voxel is set at coordinates (x, y, z)=(3, 3, 3), the detection region setter 224 sets eight voxels adjacent to the detection region Ra on the x-y plane having z=3 as a gap and sets a control region Rb in 16 voxels adjacent to these eight voxels. In addition, on both the x-y plane having z=2 and the x-y plane having z=4 that are adjacent to the x-y plane having z=3 in the z direction, the detection region setter 224 sets a voxel having coordinates of (x, y)=(3, 3) and eight voxels adjacent to the voxel as a gap and sets a control region Rb in 16 voxels adjacent to the eight voxels. Furthermore, on both the x-y plane having z=1 adjacent to the x-y plane having z=2 in the z direction and the x-y plane having z=5 adjacent to the x-y plane having z=4 in the z direction, the detection region setter 224 sets a control region Rb in all the voxels. In accordance with this, as shown in FIG. 8F, a control region Rb is set with being separate by at least one voxel apart on the periphery of the detection region Ra in a three-dimensional space.

In addition, the detection region setter 224 may dispose a gap also between control regions Rb. In other words, the detection region setter 224 may set a plurality of control regions Rb apart from each other. FIGS. 9A to 9E are diagrams showing other examples of a setting position of a detection region Ra. For example, in a case in which a detection region Ra having the same volume as that of one voxel is set at the coordinates of (x, y, z)=(3, 3, 3), the detection region setter 224 sets eight voxels adjacent to the detection region Ra on the x-y plane having z=3 as gaps and sets control regions Rb in eight voxels having coordinates of (x, y)=(1, 1), (1, 3), (1, 5), (3, 1), (3, 5), (5, 1), (5, 3), and (5, 5) among 16 voxels respectively adjacent to these eight voxels. In addition, the detection region setter 224 does not set a control region Rb on both the x-y plane having z=2 and the x-y plane having z=4 that are adjacent to the x-y plane having z=3 in the z direction but sets control regions Rb in nine voxels having coordinates of (x, y)=(1, 1), (1, 3), (1, 5), (3, 1), (3, 3), (3, 5), (5, 1), (5, 3), and (5, 5) on both the x-y plane having z=1 adjacent to the x-y plane having z=2 in the z direction and the x-y plane having z=5 adjacent to the x-y plane having z=4 in the z direction. In this way, in the three-dimensional space, the control regions Rb are set with being separate by one voxel on the periphery of the detection region Ra, and gaps may be disposed also between the control regions Rb.

Figure 10:
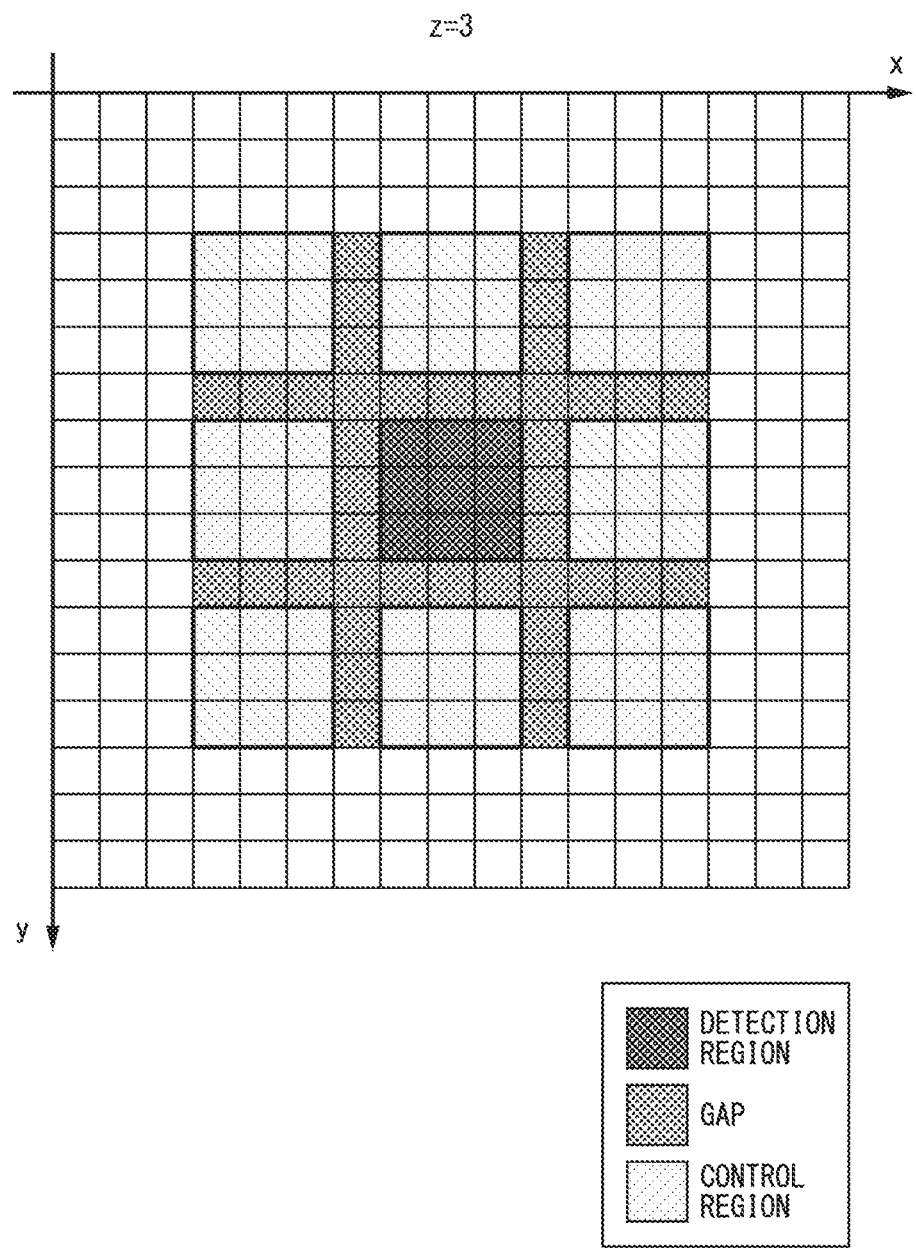
FIG. 10 is a diagram showing another example of a setting position of a detection region Ra.

In addition, the detection region setter 224 may set a detection region Ra having the same volume as that of a plurality of voxels. FIG. 10 is a diagram showing another example of a setting position of a detection region Ra. As in the example shown in the drawing, the detection region setter 224 may set a detection region Ra having the same volume as that of nine voxels. In such a case, the detection region setter 224 may set a control region Rb, which is set with a gap being interposed between the detection region Ra and the control region Rb, to have also a volume matching nine voxels.

Figure 11:
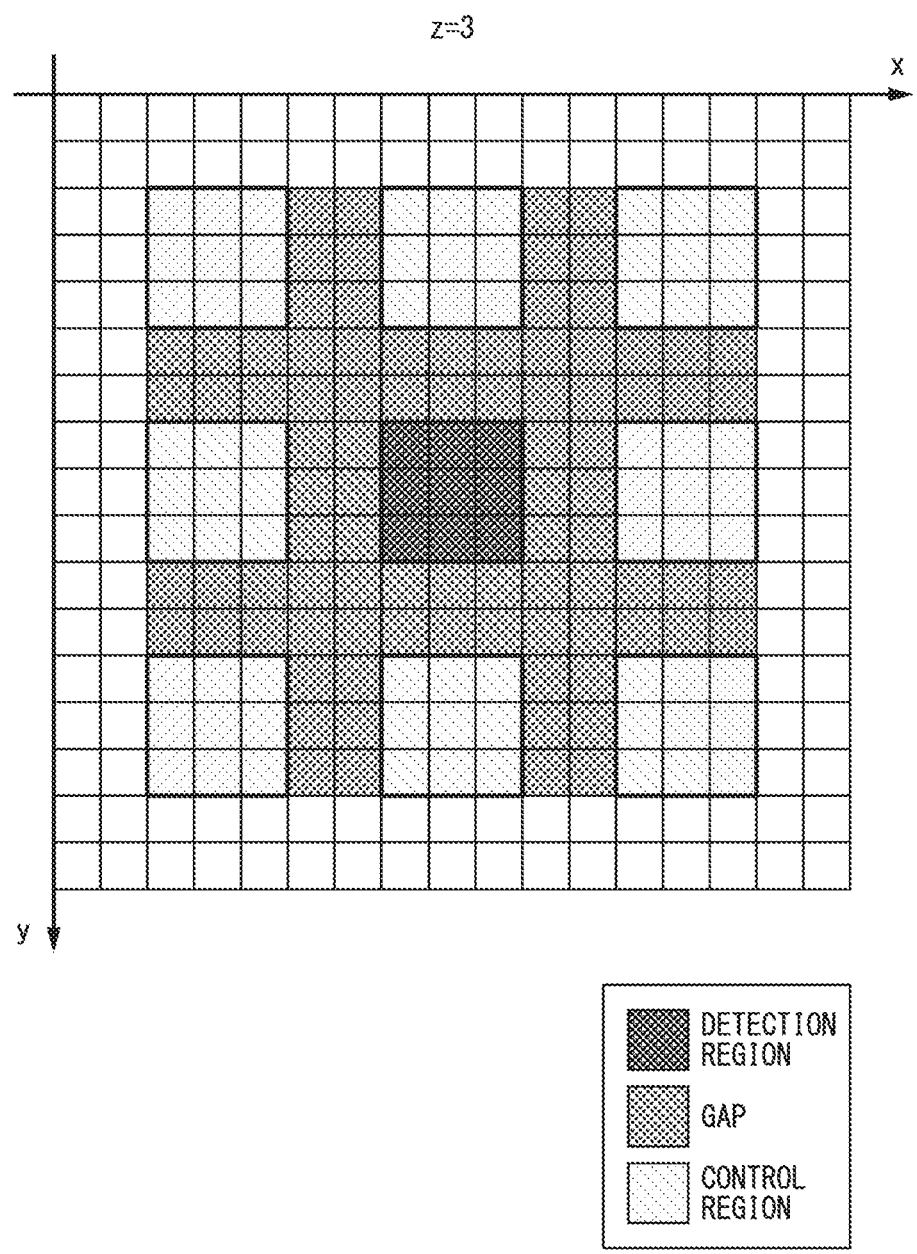
FIG. 11 is a diagram showing one example of a control region Rb set with a gap corresponding to a plurality of voxels disposed.
Figure 12:
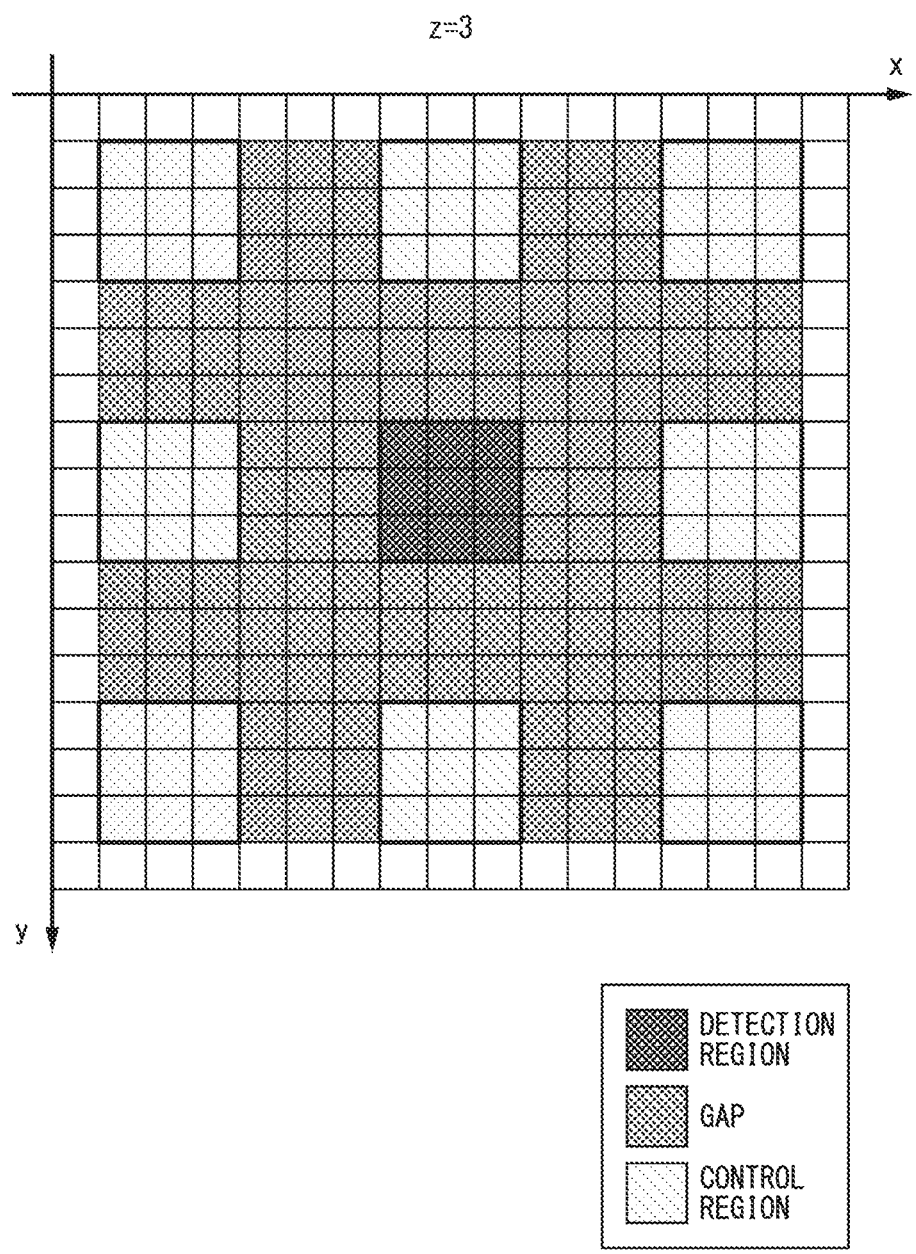
FIG. 12 is a diagram showing one example of a control region Rb set with a gap corresponding to a plurality of voxels disposed.

In addition, the detection region setter 224 is not limited to dispose a gap corresponding to one voxel but may dispose a gap corresponding to two or three or more voxels. FIGS. 11 and 12 are diagrams showing one example of a control region Rb set with a gap corresponding to a plurality of voxels disposed. In the example shown in FIG. 11, a gap corresponding to two voxels is disposed. In the example shown in FIG. 12, a gap corresponding two voxels is disposed.

Figure 13:
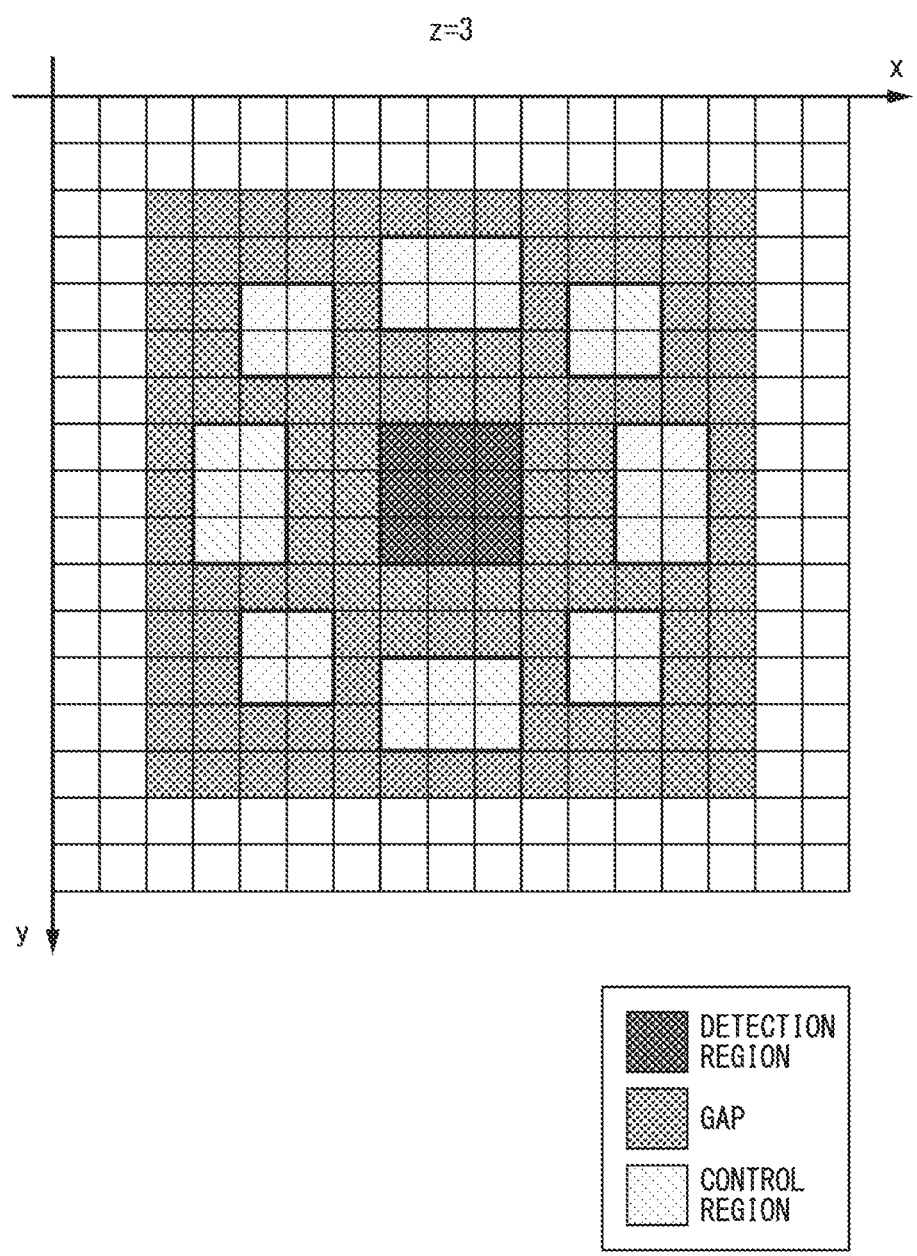
FIG. 13 is a diagram showing one example of control regions Rb arranged in a circular ring shape.
Figure 14:
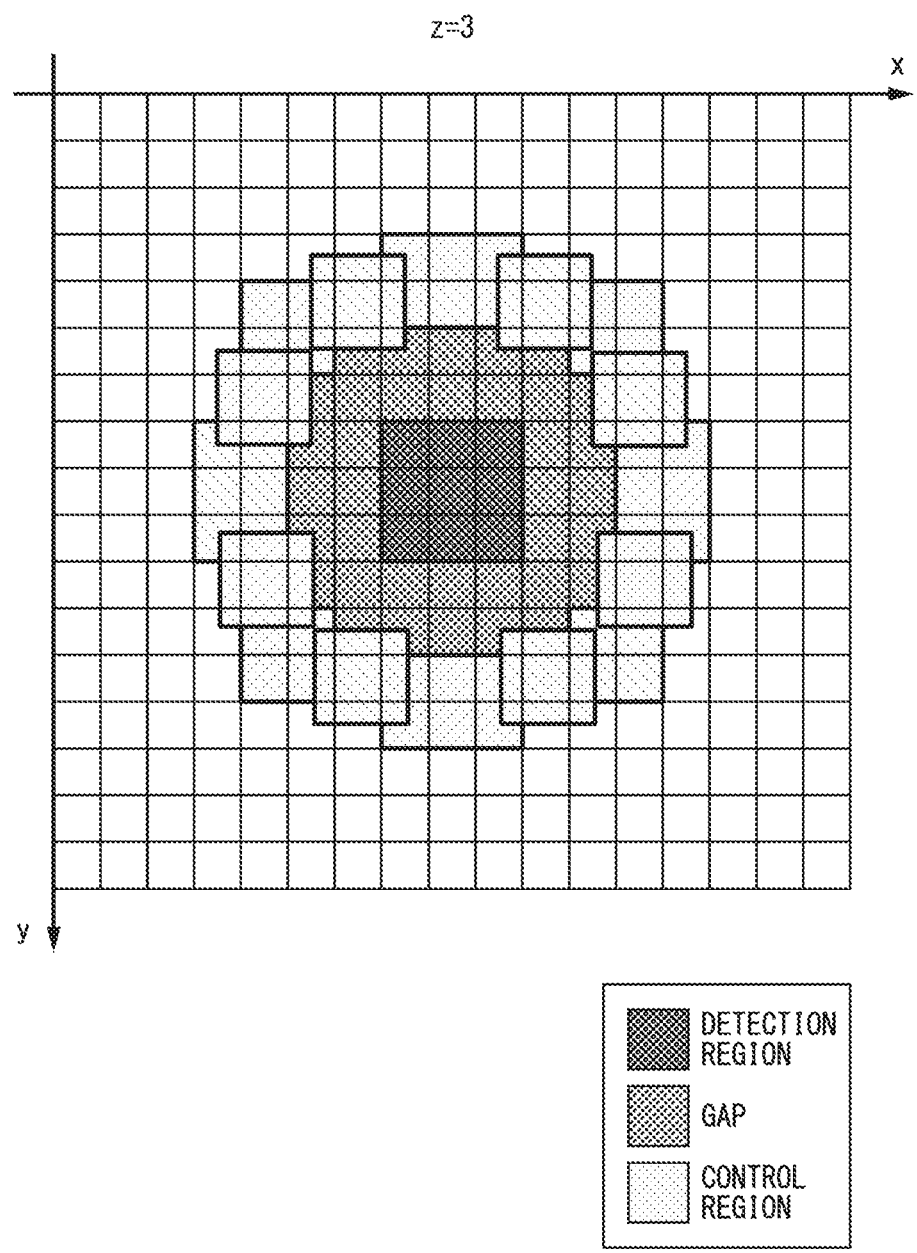
FIG. 14 is a diagram showing one example of control regions Rb arranged in a circular ring shape.

In addition, although the detection region setter 224 has been described to arrange the control regions Rb in a rectangular shape when the control regions Rb are set on the periphery of the detection region Ra, the shape is not limited thereto, and the control regions may be arranged in a circular ring shape. FIGS. 13 and 14 are diagrams showing one example of control regions Rb arranged in a circular ring shape. As in the example shown in FIG. 13, the detection region setter 224 may arrange eight control regions Rb in a circular ring shape while disposing gaps for a detection region Ra. In addition, as in the example shown in FIG. 14, the detection region setter 224 may set a plurality of control regions Rb such that the control regions Rb partly overlap each other. In accordance with this, a control region Rb that is apparently continuous one area is set on the periphery of the detection region Ra.

In addition, although the detection region setter 224 has been described to set a plurality of control regions Rb on the periphery of the detection region Ra, the setting is not limited thereto, and one control region Rb surrounding the detection region Ra may be set.

In addition, in the examples shown in FIGS. 10 to 12 and 14, although the detection region setter 224 sets a gap on the inner side of the control region Rb, as shown in FIG. 13, a gap may be set to protrude to the outside of the control region Rb to some degrees.

Figure 15:
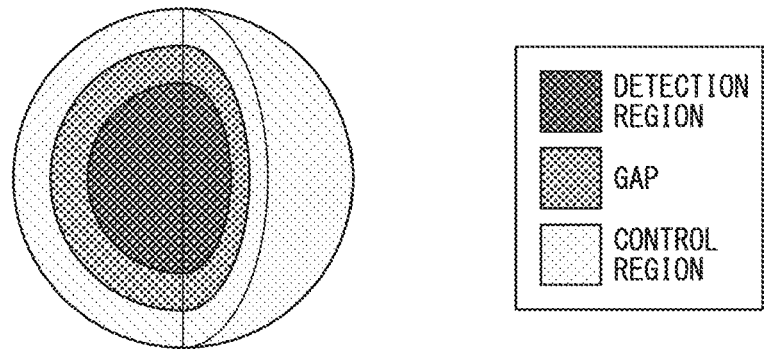
FIG. 15 is a diagram showing one example of a detection region Ra surrounded by a single control region Rb.

FIG. 15 is a diagram showing one example of a detection region Ra surrounded by a single control region Rb. As shown in the drawing, for example, the detection region setter 224 may set a detection region Ra having a sphere shape and set a control region Rb similarly having a sphere shape with a gap disposed on the periphery thereof. For example, the detection region setter 224 may set a length of the inner circumference of the control region Rb with a thickness corresponding to a gap taken into consideration for an outer circumference of the detection region Ra. In accordance with this, the control region Rb is set to surround the detection region Ra in all the directions of 360°.

Figure 16:
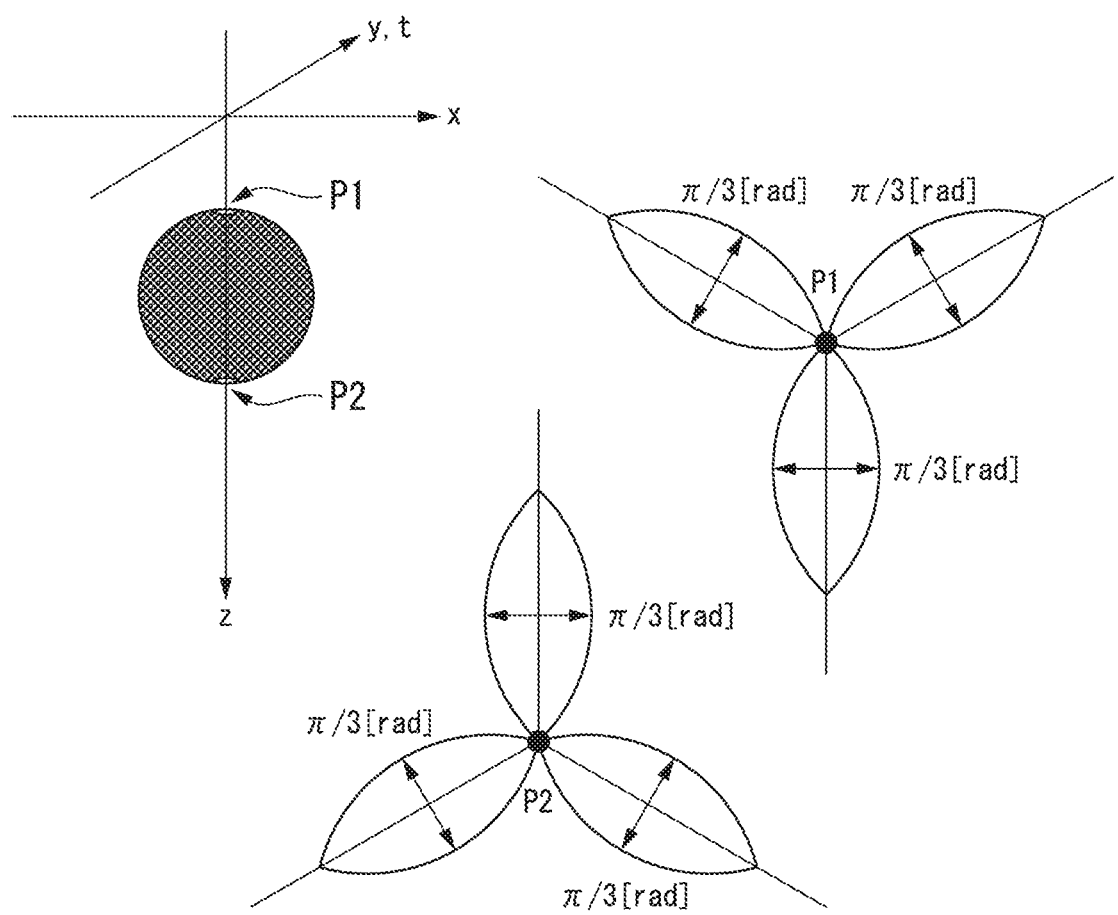
FIG. 16 is a diagram showing another example of a method of setting a control region Rb.

In addition, in a case in which a detection region Ra having a sphere shape is set, the detection region setter 224 may set a control region Rb as shown in FIG. 16. FIG. 16 is a diagram showing another example of a method of setting a control region Rb. As shown in the drawing, in a case in which a detection region Ra has a sphere shape, control regions Rb having three arc-shaped areas as one set may be set at respective intersections P1 and P2 at which a center axis of the detection region Ra having the sphere shape in the z direction and the detection region Ra intersect each other. In other words, the detection region setter 224 may set control regions Rb each dividing an upper side of the sphere shape into three parts or dividing a lower side into three parts. At this time, in a case in which a distance from the center of the detection region Ra having the sphere shape to an outer circumferential surface of a gap is A [m], a length of an arc of an inner circumferential surface of each of the control regions Rb may be at least $\pi/3$ [rad]×A [m].

Next, the index value calculator 226 calculates a maximum voxel value A of the detection region Ra set by the detection region setter 224 (Step S108). The maximum voxel value A is a voxel value taking a maximum among voxel values associated with one or more voxels included in the detection region Ra.

Next, the predetermined area determiner 228 determines whether or not the maximum voxel value A is equal to or larger than a maximum voxel threshold THa that is a threshold determined in advance (Step S110). In a case in which it is determined that the maximum voxel value A is smaller than the maximum voxel threshold THa, the predetermined area determiner 228 determines that none of one or more voxels included in the detection region Ra is a predetermined area (Step S112). The maximum voxel value A is one example of a "second threshold".

On the other hand, in a case in which it is determined that the maximum voxel value A is equal to or larger than the maximum voxel threshold THa, the index value calculator 226 calculates an average voxel value B in the detection region Ra (Step S114). The average voxel value B is an average of voxel values associated with one or more voxels included in the detection region Ra. The average voxel value B is one example of a "first average value".

Next, the predetermined area determiner 228 determines whether or not the average voxel value B is equal to or larger than an average voxel threshold THb that is a threshold determined in advance (Step S116). For example, the average voxel threshold THb is a value smaller than the maximum voxel threshold THa. In a case in which it is determined that the average voxel value is smaller than the average voxel threshold THb, the predetermined area determiner 228 causes the process to proceed to S112 and determines that none of one or more voxels included in the detection region Ra is a predetermined area. The average voxel threshold THb is one example of a "third threshold".

On the other hand, in a case in which it is determined that the average voxel value B is equal to or larger than the average voxel threshold THb, the index value calculator 226 calculates an average voxel value C in each of one or more control regions Rb set in the process of S106 (Step S118). The average voxel value C is an average of voxel values associated with one or more voxels included in the control region Rb. The average voxel value C is one example of a "second average value".

Next, the predetermined area determiner 228 determines whether or not a value (B–C) acquired by subtracting the average voxel value C from each average voxel value B is equal to or larger than a differential voxel threshold THc (Step S120). For example, the differential voxel threshold THc is a value smaller than the average voxel threshold THb. The differential voxel threshold THc is one example of a "first threshold".

For example, in a case in which it is determined that any one of differential values acquired by subtracting the average voxel value C from each average voxel value B is smaller than the differential voxel threshold THc, the predetermined area determiner 228 causes the process to proceed to the process of S112 and determines that none of one or more voxels included in the detection region Ra is not a predetermined area.

On the other hand, in a case in which it is determined that all the differential values acquired by subtracting the average voxel value C from each average voxel value B are equal to or larger than the differential voxel threshold THc, the predetermined area determiner 228 determines that all of one or more voxels included in the detection region Ra are predetermined areas (Step S122).

Next, the predetermined area determiner 228 updates a predetermined area flag corresponding to the coordinates of each of one or more voxels included in the detection region Ra in the scanning position information 214 (Step S124).

For example, in a case in which it is determined that a voxel of the detection region Ra is not a predetermined area in the process of S112, the predetermined area determiner 228 sets the predetermined area flag of the voxel of the detection region Ra to "0" in the scanning position information 214. In addition, in a case in which it is determined that a voxel of the detection region Ra is a predetermined area in the process of S122, the predetermined area determiner 228 sets the predetermined area flag of the voxel of the detection region Ra to "1" in the scanning position information 214.

Figure 17:
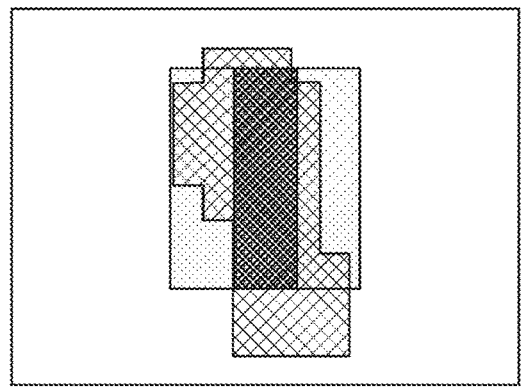
FIG. 17 is a diagram showing that determination results differ between a case in which a gap is disposed and a case in which no gap is disposed when a control region Rb is set to surround a detection region Ra.
Figure 17:
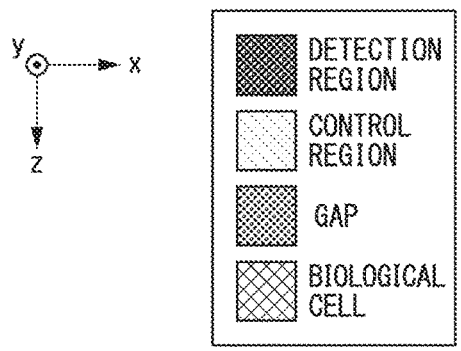
Figure 18:
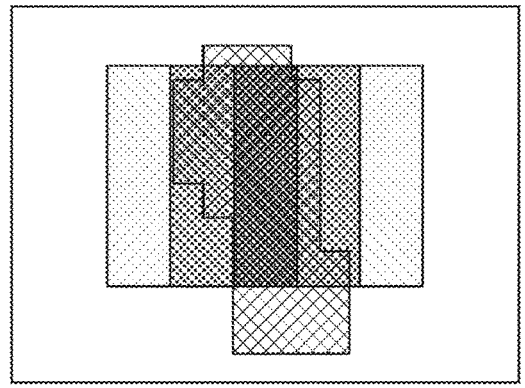
FIG. 18 is a diagram showing that determination results differ between a case in which a gap is disposed and a case in which no gap is disposed when a control region Rb is set to surround a detection region Ra.
Figure 18:
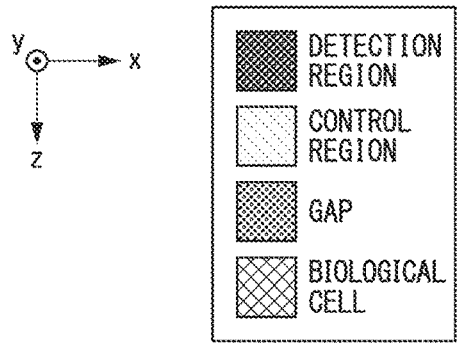

FIGS. 17 and 18 are diagrams showing that determination results are different between a case in which a gap is disposed and in a case in which no gap is disposed when a control region Rb is set to surround a detection region Ra. For example, there is a case in which a size of a biological cell, which is a detection target, in the x direction is in the same level as sizes of the detection region Ra and the control region Rb in the x direction. In such a case, as shown in FIG. 17, in a case in which no gap is disposed between the detection region Ra and the control region Rb, there is a likelihood of the biological cell, which is the detection target, overlapping both the detection region Ra and the control region Rb, a value (B−C) acquired by subtracting the average voxel value C of the control region Rb from the average voxel value B of the detection region Ra may be easily caused to be smaller than the differential voxel threshold THc, and the detection region Ra that is originally to be determined to be a predetermined area representing a biological cell may be determined not to be a predetermined area representing a biological cell. On the other hand, as shown in FIG. 18, in a case in which a gap is disposed between the detection region Ra and the control region Rb, even in a case in which a biological cell is large and overlaps also an area adjacent to the detection region Ra, the overlapping area is an area disposed as a gap. Accordingly, a value (B−C) acquired by subtracting the average voxel value C of the control region Rb from the average voxel value B of the detection region Ra may be easily caused to be equal to or larger than the differential voxel threshold THc, and a predetermined area representing a biological cell can be detected with high accuracy.

Next, the detection region setter 224 determines whether or not the detection region Ra has been set in the entire area of the space represented by the volume data 212 (Step S126). In a case in which it is determined that the detection region Ra has not been set in the entire area, the detection region setter 224 causes the process to return to the process of S104 and changes the setting position of the detection region Ra. In accordance with this, it is repeatedly determined whether a voxel of the detection region Ra of which the position has been newly changed is a predetermined area.

On the other hand, in a case in which it is determined that the detection region Ra has been set in the entire area, the cluster generator 230 generates a voxel cluster CL acquired by clustering voxels having the same level of average voxel values B among voxels of which predetermined area flag are "1" by referring to the scanning position information 214 (Step S128). Here, "voxel values being in the same level", for example, represents that a voxel value is the same as a comparison target voxel value in a range allowing error of several [%] to several tens of [%]. Accordingly, voxel values being the same is included in "voxel values being in the same level".

Figure 19:
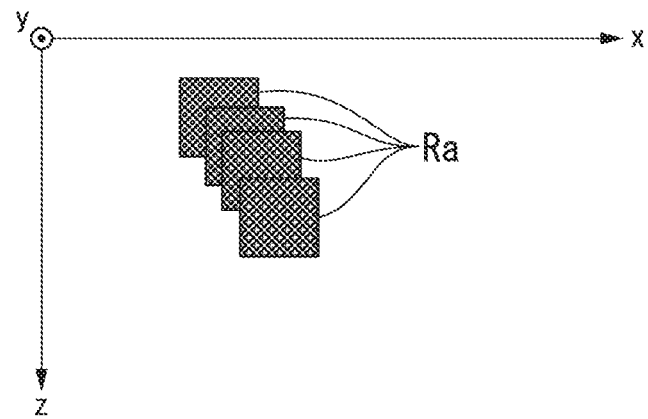
FIG. 19 is a diagram showing one example of a method of generating a voxel cluster CL.
Figure 20:
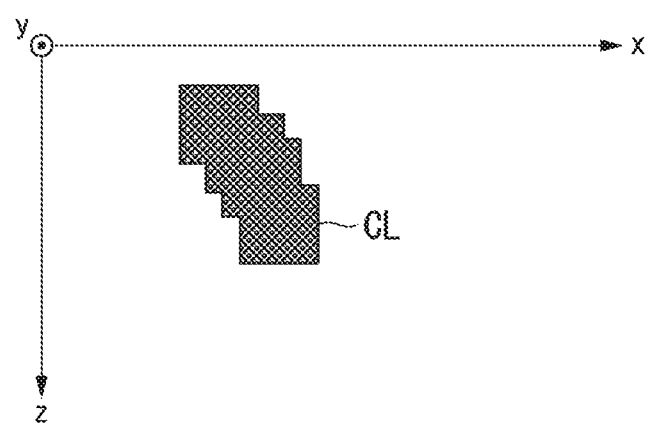
FIG. 20 is a diagram showing one example of a method of generating a voxel cluster CL.
Figure 21:
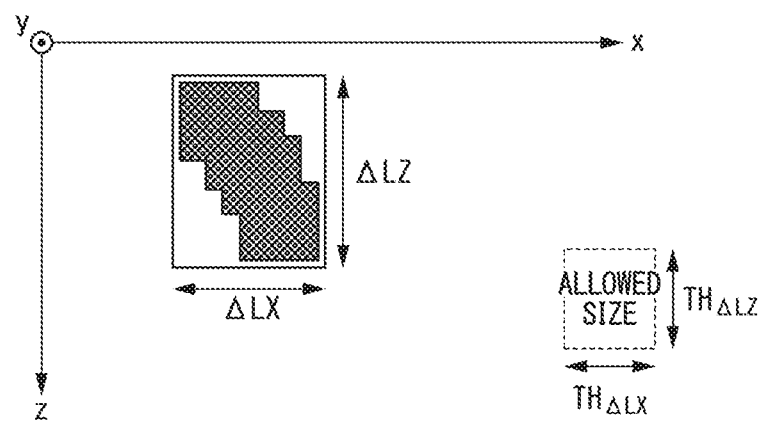
FIG. 21 is a diagram showing one example of a method of generating a voxel cluster CL.

FIGS. 19 to 21 are diagrams showing one example of a method of generating a voxel cluster CL. For example, as in the example shown in FIGS. 19 and 20, when a plurality of detection regions Ra are set, the cluster generator 230 generates one voxel cluster CL by combining regions of which average voxel values B are in the same level among a plurality of detection regions Ra through labeling processing.

For example, the cluster generator 230 selects a voxel to which a label has not been assigned yet among a plurality of voxels included in the volume data 212 as a voxel to be focused (hereinafter, referred to as a focused voxel) and assigns a certain label to the focused voxel. The cluster generator 230 determines whether or not labels have already been assigned to voxels on the periphery of the focused voxel to which the label has been assigned (for example, voxels adjacent to the focused voxel in the x, y, and z directions). In a case in which labels have not been assigned to the peripheral voxels, and the peripheral voxels have average voxel values B in the same level as that of the focused voxel, the cluster generator 230 assigns the same label as the label assigned to the focused voxel to the peripheral voxels. At this time, voxels belonging to the same voxel cluster CL are regarded to have the same voxel value (for example, an average voxel value B), and thus the same label is assigned to the voxels. The cluster generator 230 handles peripheral voxels to which labels have been assigned as new focused voxels and assigns labels to further peripheral voxels thereof by checking assignment/no-assignment of labels and voxel values for the further peripheral voxels. In this way, the cluster generator 230 assigns labels to all the voxels of the volume data 212 and generates a set of voxels, to which the same label has been assigned, having adjacent relation as one voxel cluster CL.

Next, the cluster generator 230 determines whether or not a size of the voxel cluster CL is within an allowed size (Step S130). The allowed size is a threshold set in accordance with an inspection target of the inspection system 1 and, for example, in a case in which the inspection target is a biological cell inside an eyeball E or the like, is a size that is expected by expanding or contracting an actual size of a largest biological cell assumed to be present inside the eyeball E in accordance with the resolution of the measurement device 100.

For example, as shown in FIG. 21 described above, the cluster generator 230 compares a maximum size ΔLX of the voxel cluster CL in the x direction with an allowed size TH$\Delta$LX in the x direction and compares a maximum size $\Delta$LZ of the voxel cluster CL in the z direction with the allowed size TH$\Delta$LZ in the z direction. Similarly, the cluster generator 230 compares a maximum size $\Delta$LY of the voxel cluster CL in the y direction with an allowed size TH$\Delta$LY in the y direction. In a case in which the maximum size $\Delta$LX is equal to or smaller than TH$\Delta$LX, the maximum size $\Delta$LZ is equal to or smaller than TH$\Delta$LZ, and the maximum size $\Delta$LY is equal to or smaller than TH$\Delta$LY, the cluster generator 230 determines that the size of the voxel cluster CL is within the allowed size.

On the other hand, in a case in which the maximum size $\Delta$LX exceeds TH$\Delta$LX, in a case in which the maximum size $\Delta$LZ exceeds TH$\Delta$LZ, or in a case in which the maximum size $\Delta$LY exceeds TH$\Delta$LY, the cluster generator 230 determines that the size of the voxel cluster CL is not within the allowed size. In addition, in a case in which any one of the maximum sizes $\Delta$LX, $\Delta$LZ, and $\Delta$LY is equal to or smaller than respective allowed sizes, the cluster generator 230 may determine that the size of the voxel cluster CL is within the allowed size.

When the size of the voxel cluster CL is not within the allowed size, the cluster generator 230 determines that a predetermined area represented by the voxel cluster CL is a target object (for example, an iris or the like) other than an extraction target object (for example, a biological cell) and changes the predetermined area flags associated with the plurality of voxels that are the source of the voxel cluster CL from "1" to "0" (Step S132). Accordingly, a result of determination of being a predetermined area for the plurality of voxels that are sources of the voxel cluster CL is discarded, and the plurality of voxels are regarded as not being a predetermined area. On the other hand, when the size of the voxel cluster CL is within the allowed size, the voxel cluster CL is detected as a biological cell.

Next, the cluster generator 230 calculates the number of voxel clusters CL for which the result of determination of being a predetermined area has not been discarded, in other words, the number of detected biological cells (Step S134).

Next, the controller 220 determines whether or not the series of clustering processes from S128 to S134 have been performed for the entire area of the volume data 212 (Step S136). In a case in which it is determined that the clustering processes as one example described above have not been performed for the entire area of the volume data 212, the controller 220 causes the process to return to the process of S28.

On the other hand, in a case in which it is determined that the clustering processes as one example described above have been performed for the entire area of the volume data 212, the evaluation determiner 232 evaluates the eyeball E that is a test object on the basis of the number of biological cells calculated by the cluster generator 230 (Step S138).

For example, the evaluation determiner 232 refers to the number of biological cells for each piece of volume data 212 and may determine an evaluation result representing that "there is a likelihood of an examinee having a specific disease (for example, inflammation of the cornea)" in a case in which the number of biological cells is larger than a criterion value. For example, the criterion value may be appropriately determined on the basis of a correlation result between the number of observed biological cells and outbreak of a specific disease and the like.

Next, the display controller 234 causes the display 204 to display an image based on the evaluation result according to the evaluation determiner 232 (Step S140). In accordance with this, the process of this flowchart ends.

Figure 22:
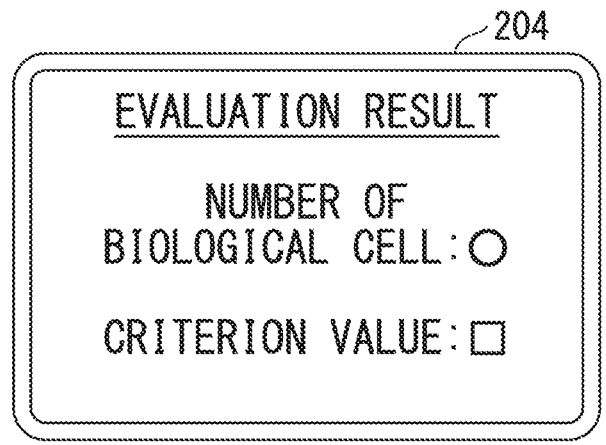
FIG. 22 is a diagram showing one example of a display 204 in which an image based on an evaluation result according to an evaluation determiner 232 is displayed.

FIG. 22 is a diagram showing one example of the display 204 in which an image based on an evaluation result according to the evaluation determiner 232 is displayed. For example, the display controller 234 may display an evaluation result including the number of biological cell, a criterion value of the number of biological cells, and presence/absence (or a probability) of a specific disease by controlling the display 204. In addition, the display controller 234 may display extracted biological cells with being superimposed on the extraction positions on one cross section (for example, a cross-sectional image having the largest number of biological cells) of the volume data 212. By causing the display 204 to display such an image, the influence of dependency on experiences, skills, and the like of individual image readers (for example, doctors or the like), in other words, the influence of individual variations is decreased, and a doctor and the like can be supported to give a stable diagnosis result based on quantitative and objective numerical values. In addition, the display controller 234 may cause the display 204 to display an image in which the number of biological cells calculated by the cluster generator 230 and one cross section of the volume data 212 that is a calculation source are associated with each other. In accordance with this, a test body can be objectively evaluated for at least the number of biological cells.

According to the first embodiment described above, by including the acquirer 222 that acquires the volume data 212 in which a physical quantity is associated with each voxel acquired by dividing a three-dimensional space, a three-dimensional time space, or a four-dimensional time space, the detection region setter 224 that sets a detection region Ra in a time space of three or more dimensions in a space or a time space represented by the volume data 212 and sets a control region Rb at a position surrounding a gap with the gap surrounding the detection region Ra disposed in a space having the same dimensions as those of the detection region Ra, and the predetermined area determiner 228 that determines whether or not one or more voxels included in the detection region Ra is a predetermined area on the basis of comparison between physical quantities of one or more voxels included in the detection region Ra and the control region Rb, the accuracy of detection of the target object can be improved.

Second Embodiment

Hereinafter, a second embodiment will be described. In the second embodiment, an eyeball E that is a test body is evaluated on the basis of a plurality of pieces of volume data 212 of which scanning times (observation times) are different from each other, which is different from the first embodiment. Hereinafter, points different from the first embodiment will be focused in description, and description of parts common to the first embodiment will be omitted.

An inspection system 1 according to the second embodiment acquires a plurality of pieces of volume data 212 that are continuous in a time series, for example, by observing aqueous humor of an eyeball E into which micro particles (for example, microbeads that are markers or the like) that are harmless to a body have been injected every time a predetermined time elapses. In other words, in the second embodiment, four-dimensional volume data 212 in which a time t dimension is added to three dimensions of x-y-z is acquired.

For example, in the second embodiment, an area in which micro particles are present is handled as a predetermined area. In this case, an evaluation determiner 232 evaluates an eyeball E that is a test object on the basis of the amount of movement of a voxel cluster CL (in other words, a micro particle), of which a size is within an allowed size, among voxel clusters CL generated by a clustering process of a cluster generator 230 according to the elapse of time.

Generally, the aqueous humor is known to flow, and a high likelihood of glaucoma is diagnosed in a case in which the flowability of the aqueous humor is low. Accordingly, the evaluation determiner 232 determines presence/absence of a symptom of glaucoma or the like in accordance with movement of a micro particle injected into the inside of the anterior chamber according to the elapse of time.

Figure 23:
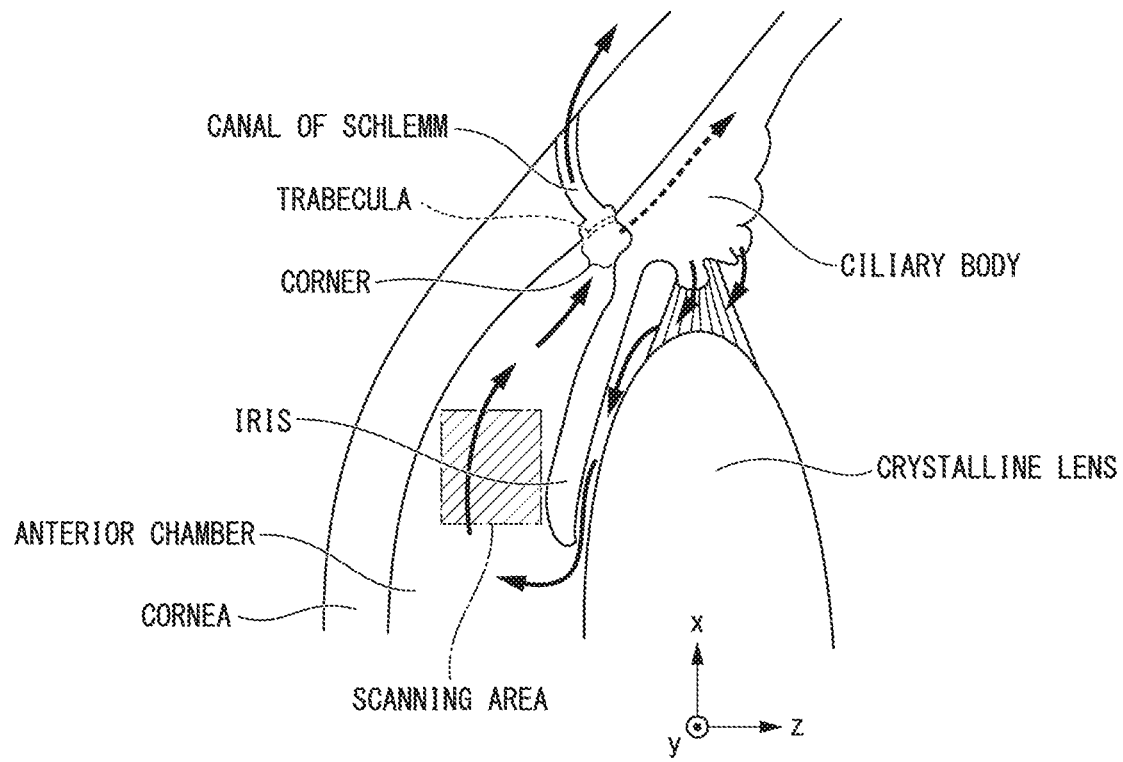
FIG. 23 is a diagram schematically showing a cross section of an eyeball E.

FIG. 23 is a diagram schematically showing a cross section of an eyeball E. Generally, a aqueous humor flows through a flowing path denoted by arrows in the drawing, for example, is secreted from a fluid ciliary epithelium to a posterior chamber and moistens a crystalline lens, then flows to an anterior chamber through a pupil, is condensed at the canal of Schlemm from a corner part (an angle of the anterior chamber) formed by an iris attachment part and a cornea through a gap of trabeculum (a Fontana's space), and flows toward tributaries of the anterior ciliary veins. In addition, there are cases in which a part of aqueous humor is absorbed through a base part of an iris from the anterior chamber. In this way, by flowing inside the eyeball E, the aqueous humor relates to nutrition of a crystalline lens, an iris, a cornea, and the like and maintains the shape of the eyeball E by maintaining an intraocular pressure to be constant. However, when an abnormality of the function of discharging aqueous humor or the like is caused, there is a case in which the aqueous humor is excessively accumulated inside the anterior chamber. In such a case, a state in which an intraocular pressure becomes unusually high is formed, and glaucoma may easily occur.

In this way, since there is a cause and effect relationship between the fluidability of the aqueous humor and glaucoma, the evaluation determiner 232 observes movement of a micro particle from the four-dimensional volume data 212 and evaluates the fluidability of the aqueous humor.

Figure 24A:
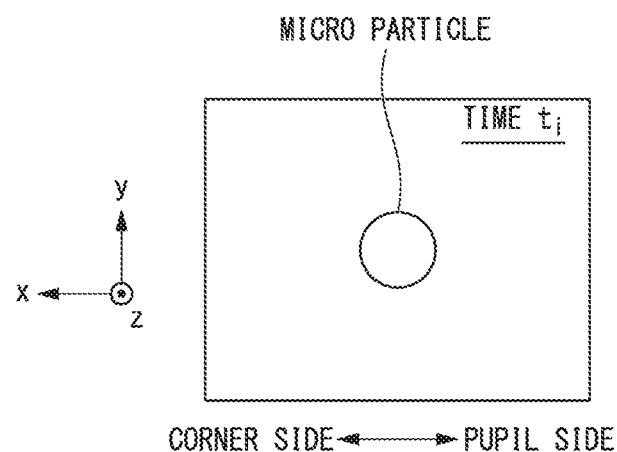
FIG. 24A is a diagram showing one cross section of two pieces of volume data 212 of which observation times differ from each other.
Figure 24B:
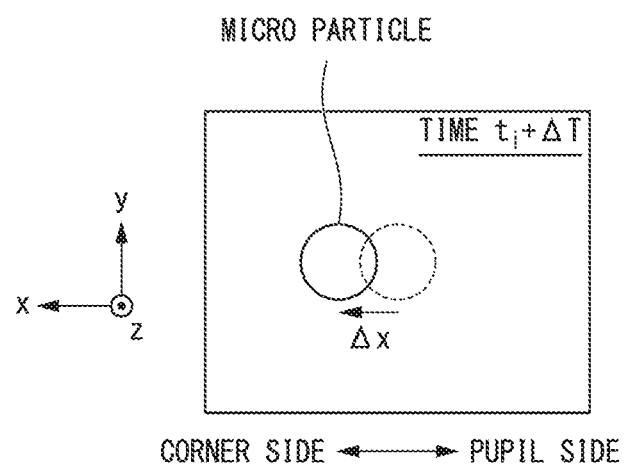
FIG. 24B is a diagram showing one cross section of two pieces of volume data 212 of which observation times differ from each other.

FIGS. 24A and 24B are diagrams showing one cross section of two pieces of volume data 212 of which observation times are different from each other. FIG. 24A shows a micro particle observed on the x-y plane at a certain time $t_i$, FIG. 24B shows a micro particle observed on the x-y plane at a time $t_i+\Delta T$ when a predetermined time $\Delta T$ elapses from the certain time $t_i$. In a case in which FIG. 24A and FIG. 24B are compared with each other, the micro particle is moving from the position of the time $t_i$ in the x axis direction with a display amount of $\Delta x$ at the time $t_i+\Delta T$. For example, the evaluation determiner 232 determines whether or not the display amount of the micro particle per a predetermined time $\Delta T$ is smaller than a threshold, determines that the micro particle stays at the same position in a case in which the displacement amount of the micro particle is smaller than the threshold, and determines that micro particle is flowing without staying at the same position in a case in which the displacement amount of the micro particle is equal to or larger than the threshold. Then, the display controller 234 causes the display 204 to display an image based on a result of the evaluation according to the evaluation determiner 232. In accordance with this, an image reader can determine a result of diagnosis of a symptom of glaucoma or the like quantitatively and objectively in accordance with flowing/non-flowing of the aqueous humor and the magnitude of the flowing.

According to the second embodiment described above, presence/absence of movement of a target object detected as a predetermined area according to elapse of time and the amount thereof are acquired on the basis of the volume data 212 of four or more dimensions, and therefore, the eyeball E that is a test body can be evaluated more quantitatively and objectively.

Third Embodiment

Hereinafter, a third embodiment will be described. In the first and second embodiments, as a device that generates the volume data 212, the measurement device 100 that emits laser light to the anterior chamber and measures a biological cell inside the anterior chamber has been described to be included. In contrast to this, in the third embodiment, as a device that generates the volume data 212, an optical coherence tomographic imaging device (hereinafter, referred to as an OCT imaging device) is included instead of the measurement device 100, which is different from the first and second embodiments. Hereinafter, points different from the first and second embodiments will be focused in description, and description of parts common to the first and second embodiments will be omitted.

Figure 25:
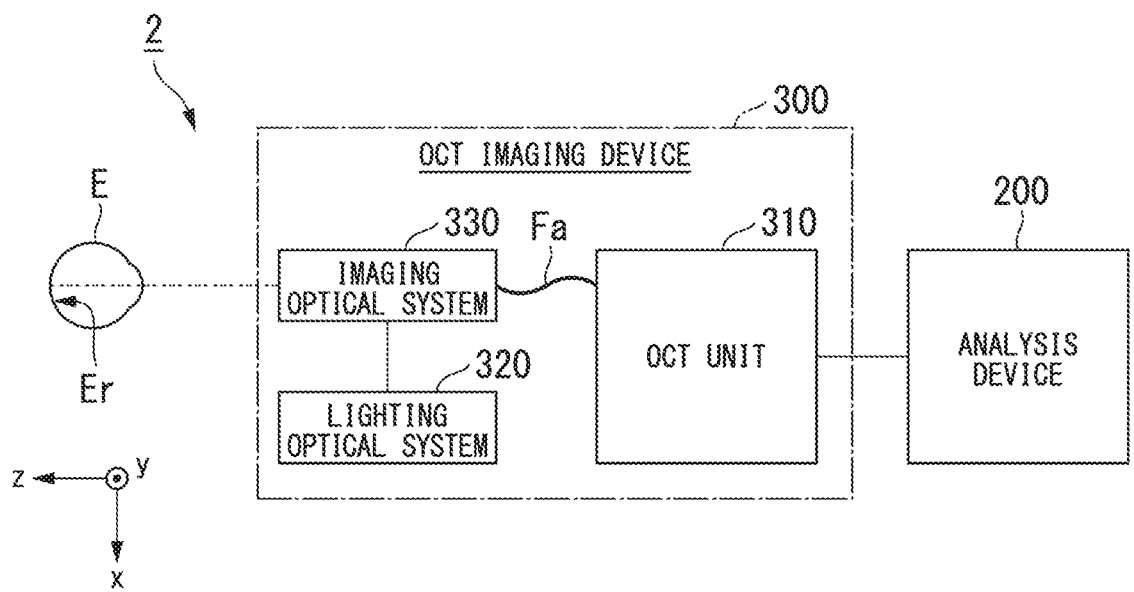
FIG. 25 is a diagram showing one example of the configuration of an inspection system 2 according to a third embodiment.

FIG. 25 is a diagram showing one example of the configuration of an inspection system 2 according to the third embodiment. The inspection system (a fundus imaging system) 2 according to the third embodiment, for example, includes an analysis device 200 and an OCT imaging device 300. The OCT imaging device 300 emits light to an eyeball E and measures interference light acquired by reflected light of the light and a part of the emitted light interfering with each other, thereby measuring a displacement of the inside of the eyeball E. In accordance with this, for example, an OCT image IM in which an eye fundus Er including a retina is projected is acquired as the volume data 212. Hereinafter, the OCT imaging device 300 will be described as a Fourier-domain OCT (FD-OCT) such as a spectral-domain OCT (SD-OCT) or a swept-source OCT (SS-OCT) but is not limited thereto. The OCT imaging device 300, for example, may employ a time-domain OCT (TD-OCT) or any other system.

For example, the analysis device 200 according to the third embodiment extracts a high-luminance part such as a hyperreflective foci (HRF) from an OCT image IM generated by the OCT imaging device 300. For example, the HRF is mentioned to represent a lipoprotein or a macrophage, and there are academic reports indicating that there is a relation between the number of HRFs observed from an OCT image of an eyeball of a patient having diabetic retinopathy and a visual performance of the patient. In the third embodiment, a predetermined area is defined as an area in which a high-luminance part such as an HRF or the like is present.

A lighting optical system 320, for example, includes a light source for illumination (not shown in the drawing) such as a halogen lamp or a xenon lamp and projects an eye fundus Er by guiding light emitted from this light source to the eye fundus Er.

An imaging optical system 330 guides reflective light reflected on the eye fundus Er to an OCT unit 310 side through an optical fiber Fa. In addition, the imaging optical system 330 guides the emitted light to the eyeball E while scanning the emitted light guided from the OCT unit 310 through the optical fiber Fa. For example, the imaging optical system 330 includes a collimator, a galvanometer mirror (both not shown in the drawing), and the like and changes an emission direction (the z direction in the drawing) of emission light emitted to the eyeball E to a horizontal direction (the x direction or the y direction in the drawing) orthogonal to the emission direction. In other words, the imaging optical system 330 scans the emission light using a raster scanning system. In accordance with this, the emission light emitted to the eyeball E is scanned in the x direction and the y direction.

An acquirer 222 of the analysis device 200 acquires an OCT image IM from the OCT imaging device 300 through a communication interface 202 and stores the acquired OCT image IM in a storage 210 as volume data 212.

Figure 26:
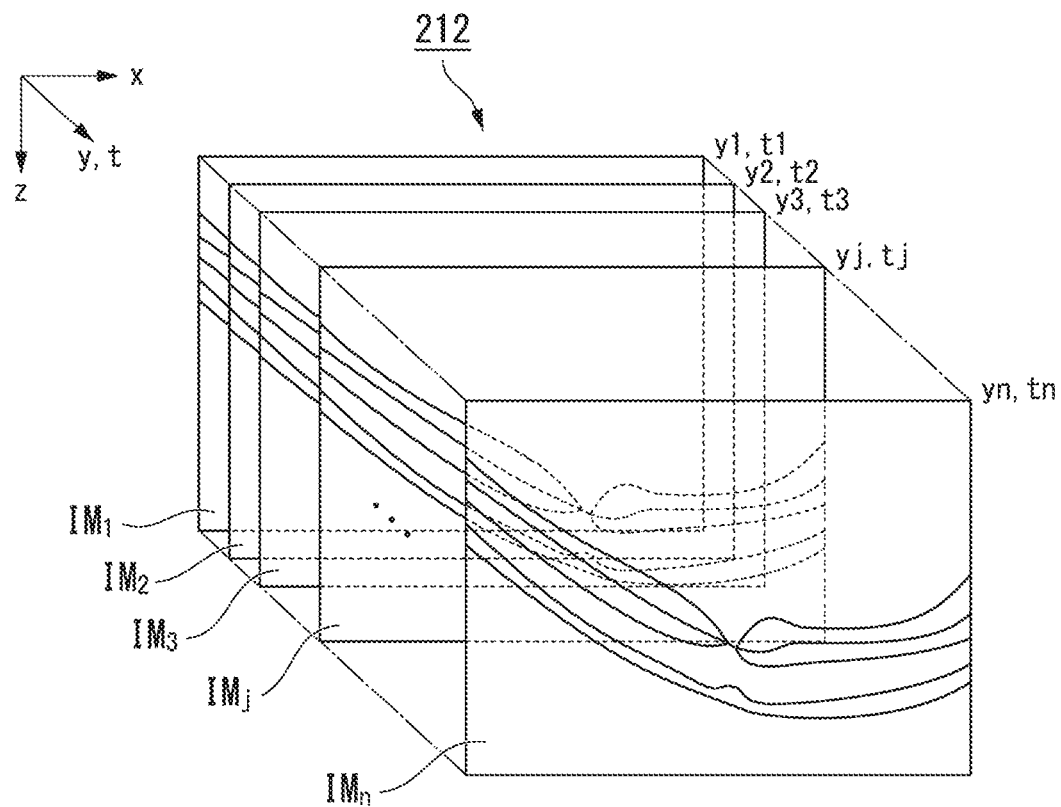
FIG. 26 is a diagram showing one example of volume data 212 generated by an OCT imaging device 300.

FIG. 26 is a diagram showing one example of volume data 212 generated by the OCT imaging device 300. As shown in the drawing, the volume data 212 according to the third embodiment is composed of a plurality of OCT images IMn (here, n is an arbitrary natural number). The z direction of each OCT image IMj (here $1 \leq j \leq n$) represents a direction along the emission direction of emitted light (an optical axis of the emitted light) and represents a depth direction of the eyeball E. The direction along the emission direction of the emitted light, for example, is a direction that is allowed to have error (an angle width) of several degrees to several tens of degrees with respect to the optical axis of the emitted light. In addition, the x direction of each OCT image IMj represents any one direction of a plane orthogonal to the z direction. Such OCT images IMn are aligned in a y direction that is orthogonal to both the z direction and the x direction. The y direction corresponds to an imaging time t of each OCT image IM. In other words, OCT images IM are aligned in an order of imaging time.

In addition, the acquirer 222 may acquire OCT images IM from the OCT imaging device 300 one each time. In such a case, the acquirer 222 may align OCT images IM that have been sequentially acquired in the y direction by referring to the imaging time t of each OCT image IM or position information in the y direction at the time of imaging. At this time, the acquirer 222, for example, may sort the OCT images IM in the y direction as is appropriate to be in the order of a time series.

The analysis device 200 according to the third embodiment determines whether or not a voxel included in a detection region Ra is a predetermined area on the basis of the volume data 212 composed of a plurality of such OCT images IM and determines whether or not a voxel cluster CL acquired by clustering voxels is within an allowed size in a case in which there is a voxel that is the predetermined area. In a case in which the voxel cluster CL is within the allowed size, the analysis device 200 determines that the voxel cluster CL is a high-luminance part such as an HRF. In other words, the analysis device 200 determines that a high-luminance part such as an HRF is present in the eye fundus Er. The analysis device 200 calculates the number of high-luminance parts present in a space (a three-dimensional image) represented by the volume data 212 and evaluates the eyeball E that is a test object on the basis of the calculated number of high-luminance parts.

According to the third embodiment described above, a detection region Ra and one or more control regions Rb surrounding this are set in a space represented by the volume data 212 composed of a plurality of OCT images IM, it is determined whether one or more voxels included in the detection region Ra are predetermined areas (a high-luminance part such as an HRF) on the basis of comparison between physical quantities (for example, pixel values) of one or more voxels included in each of the detection region Ra and the control regions Rb. Therefore, similar to the first or second embodiment, accuracy of detection of a target object can be improved.

Other Embodiment

Hereinafter, other embodiments will be described. Although biological cells present inside the anterior chamber of the eyeball E have been described to be detected in the first and second embodiments described above, and high-luminance parts such as HRFs present in the eye fundus Er of the eyeball E have been described to be detected in the third embodiment, but the detection is not limited thereto. For example, micro objects that perform fluorescent labeling of an organ and the like or blood corpuscles or the like included in blood may be detected using the technique described above. In such a case, the volume data 212 may be acquired using various measurement devices such as an optical microscope including a fluorescent microscope, an electron microscope including a TEM, a SEM, or the like, or any other tomographic image capturing device including a CT, a PET, an MRI, an NMR, ultrasonic waves, or the like.

For example, in the field of biological imaging, labeling of cells is performed by bringing materials (hereinafter, referred to as markers) labeled for detecting predetermined antibodies into contact with cells of an organ and the like and combining the markers with the predetermined antibodies. In this case, three-dimensional volume data 212 is generated by measuring cells or organs and the like using a fluorescent microscope or the like. The analysis device 200 may detect areas in which markers are present as predetermined areas by referring to this volume data 212. The markers, for example, are fluorescent dyes such as a Fluorescein Isothiocyanate (FITC), an Alexa Fluor dye, a Cy dye, antibodies dyed using fluorescent proteins such as Phycoerythrin (PE) or Allophycocvanin (APC), or the like. In addition, the markers may be antibodies combined with enzyme or antibodies combined with carriers such as magnetic beads or agarose. By detecting areas in which such markers are present as predetermined areas from the volume data 212, for example, a place of an organ at which the markers are coagulated (dyed) can be determined.

In addition, in a case in which the volume data 212 is three-dimensional data acquired by observing the inside of blood vessels using a three-dimensional blood imaging method such as a CT blood vessel imaging method (CT angiography; CTA) or an MR blood vessel imaging method (MR angiography; MRA), the analysis device 200 may detect areas in which predetermined corpuscles are present as predetermined areas from the volume data 212 of blood vessels, or areas in which predetermined corpuscles labeled using fluorescence may be detected as predetermined areas.

Like this, in a case in which targets desired to be detected are micro objects, the present technique can be applied.

[Hardware Configuration]

Figure 27:
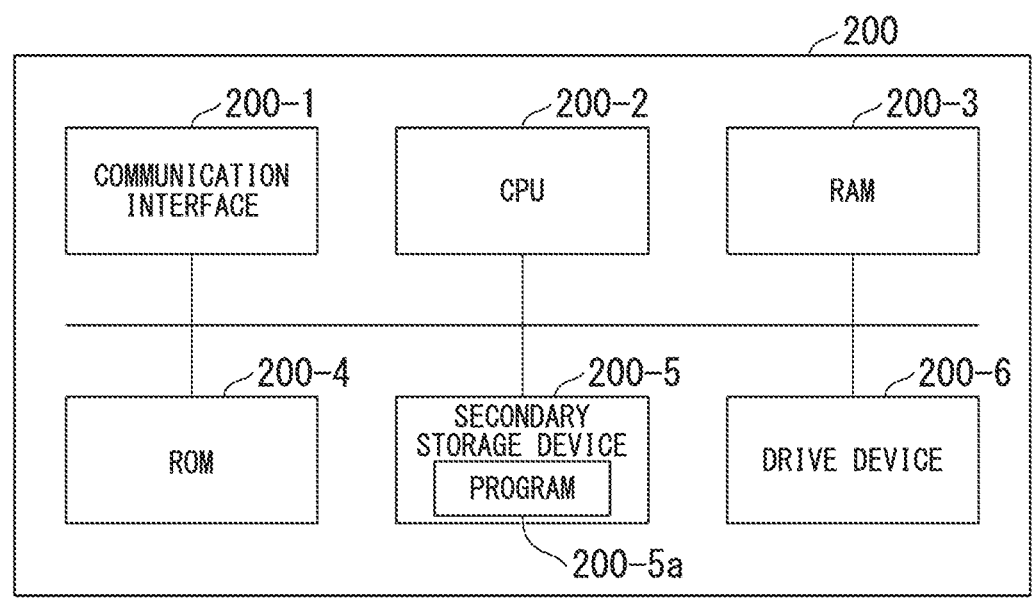
FIG. 27 is a diagram showing one example of the hardware configuration of an analysis device 200 according to an embodiment.

The analysis device 200 according to the embodiments described above, for example, is realized using a hardware configuration as shown in FIG. 27. FIG. 27 is a diagram showing one example of the hardware configuration of the analysis device 200 according to an embodiment.

The analysis device 200 has a configuration in which a communication interface 200-1 such as a network interface card (NIC), a CPU 200-2, a RAM 200-3, a ROM 200-4, a secondary storage device 200-5 such as a flash memory or an HDD, and a drive device 200-6 are interconnected using an internal bus or dedicated communication lines. A portable storage medium such as an optical disc is loaded in the drive device 200-6. A program 200-5a stored in the secondary storage device 200-5 is expanded into the RAM 200-3 by a DMA controller (not shown in the drawing) or the like and is executed by the CPU 200-2, whereby the controller 220 is realized. In addition, a program referred to by the CPU 200-2 may be stored in a portable storage medium loaded in the drive device 200-6 or may be downloaded from another device through a network.

The embodiment described above can be represented as below.

An analysis device includes a storage storing a program and a processor, and by executing the program described above processor is configured to acquire data in which a physical quantity is associated with each unit area acquired by dividing a three-dimensional space, a three-dimensional time space, or a four-dimensional time space, set a detection region in a time space of three or more dimensions in the space or the time space, set a control region at a position surrounding a gap with the gap surrounding the detection region disposed in a space having the same dimensions as those of the detection region; and determine whether or not one or more unit areas included in the detection region are predetermined areas on the basis of comparison between physical quantities of one or more unit areas included in the detection region and the control region that are set.

As above, although the forms for performing the present invention have been described using the embodiments, the present invention is not limited to such embodiments at all, and various modifications and substitutions can be applied in a range not departing from the concept of the present invention.

What is claimed is:

1. A non-transitory computer-readable storage medium storing a program to cause a computer to execute operations, the operations comprising:
    acquiring data in which a physical quantity is associated with each unit area acquired by dividing a three-dimensional space, a three-dimensional time space, or a four-dimensional time space;
    setting a detection region in a time space of three or more dimensions in the space or the time space;
    setting a control region at a position surrounding a gap with the gap surrounding the detection region disposed in a space having the same dimensions as those of the detection region; and
    determining whether or not one or more unit areas included in the detection region are predetermined areas on the basis of comparison between physical quantities of one or more unit areas included in the detection region and the control region that are set,
    wherein the determining whether or not one or more unit areas being the predetermined areas comprises:
    determining whether or not a maximum value of the physical quantities of one or more unit areas included in the detection region is equal to or larger than a second threshold; and
    determining that the one or more unit areas included in the detection region are not the predetermined areas in a case in which it is determined that the maximum value is equal to or larger than the second threshold.

2. The storage medium according to claim 1, wherein the setting the detection region comprises: setting a plurality of control regions at positions surrounding the gap.

3. The storage medium according to claim 2, wherein the setting the detection region comprises: setting the plurality of control regions apart from each other in a case in which the plurality of control regions are set.

4. The storage medium according to claim 1, wherein the setting the detection region comprises: setting the plurality of control regions adjacent to each other in a case in which the plurality of control regions are set.

5. The storage medium according to claim 1, wherein the setting the detection region comprises: setting a plurality of control regions to partly overlap each other in a case in which the plurality of control regions are set.

6. The storage medium according to claim 1, wherein the determining whether or not one or more unit areas being the predetermined areas comprises:
    determining whether or not a difference between a first average value of physical quantities of one or more unit areas included in the detection region and a second average value of physical quantities of one or more unit areas included in each of one or more control regions is equal to or larger than a first threshold; and
    determining that one or more unit areas included in the detection region are the predetermined areas in a case in which it is determined that differences between the first average value and some or all of one or more second average values are equal to or larger than the first threshold.

7. A non-transitory computer-readable storage medium storing a program to cause a computer to execute operations, the operations comprising:
    acquiring data in which a physical quantity is associated with each unit area acquired by dividing a three-dimensional space, a three-dimensional time space, or a four-dimensional time space;
    setting a detection region in a time space of three or more dimensions in the space or the time space;
    setting a control region at a position surrounding a gap with the gap surrounding the detection region disposed in a space having the same dimensions as those of the detection region; and
    determining whether or not one or more unit areas included in the detection region are predetermined areas on the basis of comparison between physical quantities of one or more unit areas included in the detection region and the control region that are set,
    wherein the determining whether or not one or more unit areas being the predetermined areas comprises:
    determining whether or not a first average value of physical quantities of one or more unit areas included in the detection region is equal to or larger than a third threshold; and
    determining that the one or more unit areas included in the detection region are not the predetermined areas in a case in which it is determined that the first average value is not equal to or larger than the third threshold.

8. The storage medium according to claim 7, wherein the setting the detection region comprises: setting a plurality of control regions at positions surrounding the gap.

9. The storage medium according to claim 8, wherein the setting the detection region comprises: setting the plurality of control regions apart from each other in a case in which the plurality of control regions are set.

10. The storage medium according to claim 7, wherein the setting the detection region comprises: setting the plurality of control regions adjacent to each other in a case in which the plurality of control regions are set.

11. The storage medium according to claim 7, wherein the setting the detection region comprises: setting a plurality of control regions to partly overlap each other in a case in which the plurality of control regions are set.

12. The storage medium according to claim 7, wherein the determining whether or not one or more unit areas being the predetermined areas comprises:
- determining whether or not a difference between a first average value of physical quantities of one or more unit areas included in the detection region and a second average value of physical quantities of one or more unit areas included in each of one or more control regions is equal to or larger than a first threshold, and
- determining that one or more unit areas included in the detection region are the predetermined areas in a case in which it is determined that differences between the first average value and some or ail of one or more second average values are equal to or larger than the first threshold.

13. A non-transitory computer-readable storage medium storing a program to cause a computer to execute operations, the operations comprising:
- acquiring data in which a physical quantity is associated with each unit area acquired by dividing a three-dimensional space, a three-dimensional time space, or a four-dimensional time space;
- setting a detection region in a time space of three or more dimensions in the space or the time space;
- setting a control region at a position surrounding a gap with the gap surrounding the detection region disposed in a space having the same dimensions as those of the detection region; and
- determining whether or not one or more unit areas included in the detection region are predetermined areas on the basis of comparison between physical quantities of one or more unit areas included in the detection region and the control region that are set, wherein the program causes the computer to further execute:
- generating a cluster acquired by forming one or more unit areas determined as the predetermined areas as one; and
- causing a display to display the number of clusters and acquired data in association with each other.

14. The storage medium according to claim 13, wherein, the setting the detection region comprises: setting a plurality of control regions at positions surrounding the gap.

15. The storage medium according to claim 14, wherein the setting the detection region comprises: setting the plurality of control regions apart from each other in a case in which the plurality of control regions are set.

16. The storage medium according to claim 13, wherein the setting the detection region comprises: setting the plurality of control regions adjacent to each other in a case in which the plurality of control regions are set.

17. The storage medium according to claim 13, wherein the acting the detection region comprises: setting a plurality of control regions to partly overlap each other in a case in which the plurality of control regions are set.

18. The storage medium according to claim 13, wherein the determining whether or not one or more unit areas being the predetermined areas comprises:
- determining whether or not a difference between a first average value of physical quantities of one or more unit, areas included in the detection region and a second average value of physical quantities of one or more unit areas included in each of one or more control regions is equal to or larger than a first threshold; and
- determining that one or more unit areas included in the detection region are the predetermined areas in a case in which it is determined that differences between the first average value and some or all of one or more second average values are equal to or larger than the first threshold.

* * * * *